(12) United States Patent
Kochergin et al.

(10) Patent No.: US 7,106,919 B2
(45) Date of Patent: Sep. 12, 2006

(54) MAGNETO-OPTICAL SENSING EMPLOYING PHASE-SHIFTED TRANSMISSION BRAGG GRATINGS

(75) Inventors: Vladimir Kochergin, Westerville, OH (US); Philip Swinehart, Westerville, OH (US)

(73) Assignee: Lake Shore Cryotronics, Inc., Westerville, OH (US)

( * ) Notice: Subject to any disclaimer, the term of this patent is extended or adjusted under 35 U.S.C. 154(b) by 254 days.

(21) Appl. No.: 10/316,192

(22) Filed: Dec. 11, 2002

(65) Prior Publication Data

US 2003/0133657 A1    Jul. 17, 2003

Related U.S. Application Data

(60) Provisional application No. 60/338,685, filed on Dec. 11, 2001.

(51) Int. Cl.
*G02B 6/00* (2006.01)
*G02B 6/34* (2006.01)

(52) U.S. Cl. ............................................ 385/12; 385/37

(58) Field of Classification Search ................ 385/12, 385/37; 324/244.1, 96; 356/351; 250/227.17; 359/282
See application file for complete search history.

(56) References Cited

U.S. PATENT DOCUMENTS

| | | | |
|---|---|---|---|
| 5,319,725 A | 6/1994 | Buchmann et al. | |
| 5,493,220 A | 2/1996 | Oliver et al. | |
| 5,631,559 A | 5/1997 | Oliver et al. | |
| 5,736,856 A | 4/1998 | Oliver et al. | |
| 5,982,174 A | 11/1999 | Wagreich | |
| 5,994,898 A * | 11/1999 | DiMarzio et al. | 324/244.1 |
| 6,143,435 A | 11/2000 | Il"Yashenko et al. | |
| 6,192,177 B1 | 2/2001 | Amundson et al. | |
| 6,233,263 B1 * | 5/2001 | Chang-Hasnain et al. | 372/32 |
| 6,262,949 B1 | 7/2001 | Inoue et al. | |
| 6,285,812 B1 | 9/2001 | Amundson et al. | |
| 6,534,977 B1 | 3/2003 | Duncan et al. | |

OTHER PUBLICATIONS

J.L. Arce-Diego, et al., "Fiber Bragg grating as an optical filter tuned by a magnetic field," *Optics Letters*, vol. 22, No. 9, pp. 603-605 (May 1, 1997).

Nobuki Itoh, et al., "Small optical magnetic-field sensor that uses rare-earth iron garnet films based on the Faraday effect," *Applied Optics*, vol. 38, No. 10, pp. 2047-2052 (Apr. 1, 1999).

Merritt N. Deeter, "Fiber-optic Faraday-effect magnetic-field sensor based on flux concentrators," *Applied Optics*, vol. 35, No. 1, pp. 154-157 (Jan. 1, 1996).

A. Yu, et al., "Practical Sagnac interferometer based fibre optic current sensor," *IEE Proc.-Optoelectron*, vol. 141, No. 4, pp. 249-256 (Aug. 1994).

M. N. Deeter, et al., "Magneto-Optic Magnetic Field Sensor With 1.4pT/ (Hz) Minimum Detectable Field at 1 kHz," *Electronics Letters*, vol. 29, No. 11, pp. 993-994 (May 27, 1993).

(Continued)

*Primary Examiner*—Frank G. Font
*Assistant Examiner*—Michael P. Mooney
(74) *Attorney, Agent, or Firm*—Nixon & Vanderhye P.C.

(57) ABSTRACT

A new fiber-optic magnetic field or current sensor design can increase the accuracy, resolution and environmental stability of the subject sensor. The design is based on phase-shifted fiber or planar waveguide Bragg grating, in which a Fabry-Perot resonator is formed around the phase shift. When the wavelength of incident light coincides with the wavelength of FP resonator mode, the magnetic field induced polarization rotation of the waveguided light will be strongly enhanced.

15 Claims, 15 Drawing Sheets

OTHER PUBLICATIONS

M. N. Deeter, et al., "Magneto-Optic Magnetic Field Sensors Based on Uniaxial Iron Garnet Films In Optical Waveguide Geometry," *IEEE Transactions on Magnetics*, vol. 29, No. 6, pp. 3402-3404 (Nov. 1993).

M.J. Steel, et al., "Large Magnetooptical Kerr Rotation with High Reflectivity from Photonic Bandgap Structures with Defects," *Journal of Lightwave Technology*, vol. 18, No. 9, pp. 1289-1296 (Sep. 2000).

M.J. Steel, et al., "Photonic Bandgaps with Defects and the Enhancement of Faraday Rotation," *Journal of Lightwave Technology*, vol. 18, No. 9, pp. 1297-1308 (Sep. 2000).

M. Vallet, et al., "The Malus Fabry-Perot interferometer," *Optics Communication 168*, pp. 423-443 (Sep. 15, 1999).

Mitsuteru Inoue et al., "Magneto-optical properties of one-dimensional photonic crystals composed of magnetic and dielectric layers," *Journal of Applied Physics*, vol. 83, No. 11, pp. 6768-6770 (Jun. 1, 1998).

Mitsuteru Inoue et al., "One-dimensional magnetophotonic crystals," *Journal of Applied Physics*, vol. 85, No. 8, pp. 5768-5770 (Apr. 15, 1999).

S. Sakaguchi et al., "Transmission Properties of Multilayer Films Composed of Magneto-Optical and Dielectric Materials," *Journal of Lightwave Technology*, vol. 17, No. 6, pp. 1087-1092 (Jun. 1999).

J. Blake, et al., "In-Line Sagnac Interferometer Current Sensor," *IEEE Transactions on Power Delivery*, vol. 11, No. 1, pp. 116-121 (Jan. 1996).

Rochford et al, "Faraday effect current sensor with improved sensitivity-bandwidth product," Optics Letters, Nov. 15, 1994, 1903-1905, vol. 19 No. 22, USA.

Day et al, "Faraday Effect Sensors for Magnetic Field and Electric Current," SPIE, 1994, 90-95, vol. 2341, USA.

Ning et al, "Recent progress in optical current sensing techniques," Rev. Sci. Instrum., May 1995, 3097-3111, vol. 66 (5), USA.

Rose, "Playing with Fire and Fibers," Circuits & Devices, Sep. 1999, 41-46, USA.

Chan et al, "Optimal sensing of current based on an extrinsic Sagnac interferometer configuration," Optics & Lasers in Engineering, 1998, 17-24, vol. 30, USA.

Bahlmann et al, "Improved Design of Magnetooptic Rib Waveguides for Optical Isolators," May 1998, 818-823, vol. 16, No. 5, USA.

Wallenhorst et al, "Enhancement of the nonreciprocal magneto-optic effect of TM modes using iron garnet double layers with opposite Faraday rotation," J. Appl. Phys., Apr. 1995, 2902-2905, vol. 77 (7), USA.

Syvorotka et al, "Growth and characterization of Bi, PR- and Bi, Sc-substituted lutetium iron garnet films with planar magnetization for magneto-optic visualization," J. Phys. D: Appl. Phys, 2001, 1178-1187, vol. 34, USA.

Kamada et al, "Magneto-optical properties of $(BiGdY)3Fe5O12$ for optical magnetic field sensors," J. Appl.Phys, Nov. 15, 1994, 6801-6803, vol. 75(10), USA.

Fisher et al, "Vibration immunity and Ampere's circuital law for a near perfect triangular Faraday current sensor," Meas.Sci.Technol, 1996, 1900-1102, vol. 79, UK.

Chang-Hasnain, "Tunable VCSEL," IEE J. on Selected Topics in Quantum Electronics, Nov./Dec. 2000, 978-987, vol. 6 No. 6, USA.

Harris, "Tunable Long-Wavelength Vertical-Cavity Lasers: The Engine of Next Generation Optical Networks?" IEEE EE J. on Selected Topics in Quantum Electronics, Nov./Dec. 2000, 1145-1160, vol. 6, No. 6, USA.

\* cited by examiner

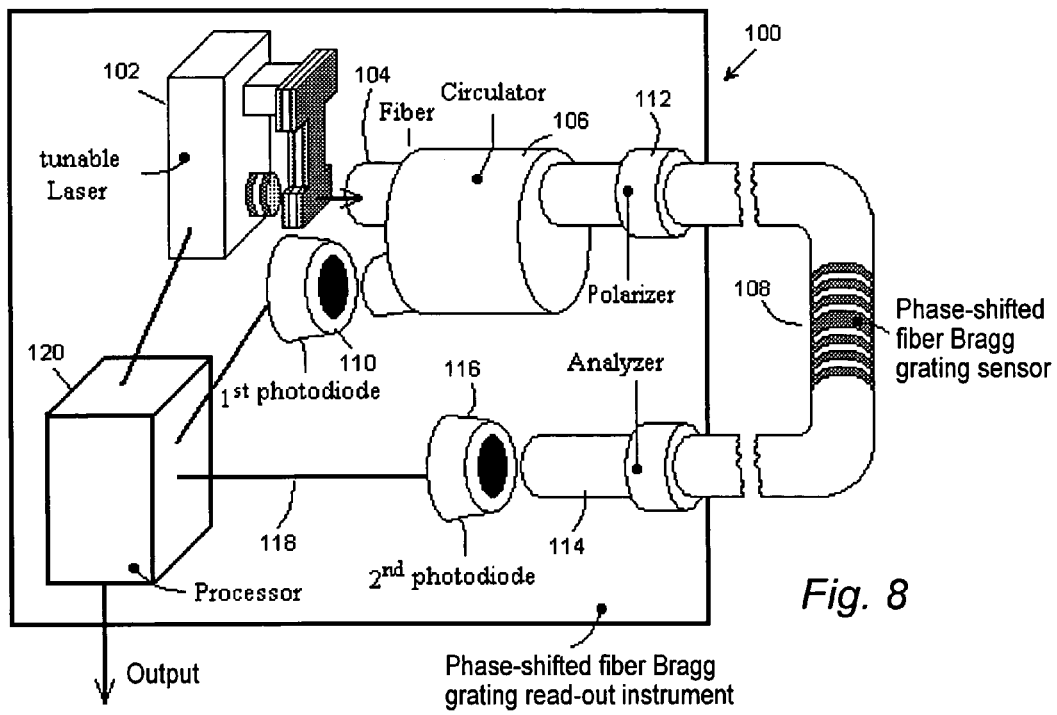
Fig. 8
Fig. 8A
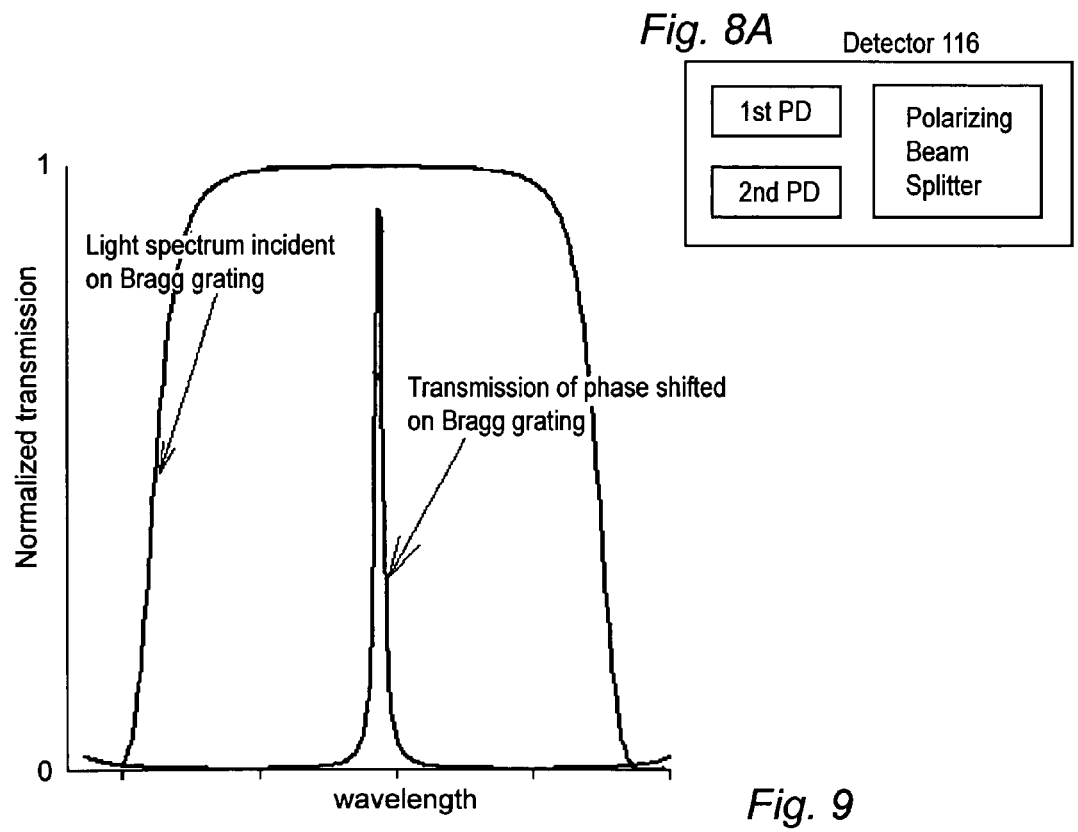
Fig. 9

MAGNETO-OPTICAL SENSING EMPLOYING PHASE-SHIFTED TRANSMISSION BRAGG GRATINGS

CROSS-REFERENCES TO RELATED APPLICATIONS

This application claims the benefit of priority from application Ser. No. 60/338,685 filed Dec. 11, 2001, incorporated herein by reference.

STATEMENT REGARDING FEDERALLY SPONSORED RESEARCH OR DEVELOPMENT

Not applicable.

FIELD OF THE INVENTION

The invention is related to fiber-optic sensing applications for magnetic fields, including magnetic fields due to electrical currents. More particularly, the invention relates to a phase-shifted fiber or waveguide Bragg grating in which a Fabry-Perot resonator is formed around the phase shift.

BACKGROUND AND SUMMARY OF THE INVENTION

Magnetic field and electrical current sensors play an important role in both military and civilian applications. Fiber optic based sensors offer many necessary and attractive benefits that have been driving their development for several decades. These benefits include immunity to electromagnetic interference (EMI), excellent electrical isolation, compatibility with modern communication networks, multiplexibility, compactness, light weight and an inherently explosion proof nature. Militarily useful attributes include resistance to lightning and nuclear blast-induced EMI, light weight for flight systems, low electronic emissions (from the sensors) and explosion proof nature for use with fuels. Potential commercial uses parallel those of the military and may be even more extensive. Tachometry, magnetometry, commercial aircraft instrumentation and petrochemicals are potential markets.

Although fiber optic magnetic field and/or electrical current sensors have been applied to a few markets, notably high voltage current sensing in the power industry, their potential advantages have sometimes been outweighed by their expense, size and lack of physical robustness. It is suitable to divide sensors according to the magneto-optical material utilized. The cheapest material is optical fiber itself. One drawback of such optical fiber sensors is the very small Faraday activity of standard optical glass. Many turns of fiber around the conductor wire or flux path helps to increase the fiber-to-magnetic field interaction length, although birefringence also accumulates per unit length and limits the sensitivity of such sensors. The higher Faraday rotation glasses are utilized in bulk form in the sensors, using multiple total internal reflections (see, e.g., Y. N. Ning et al in "Recent progress in optical current sensing techniques", *Review of Scientific Instruments* 66 (5), May 1995, pp. 3097–3111). However, such sensors generally require precise surface machining and optical alignment. By incorporating birefringence compensation, such sensors can gain up to an order of magnitude in resolution. See e.g., N. E. Fisher & D. A. Jackson, Meas. Sci. Technol. 7 (1996)p 1099–1102, but mechanical and environmental stability, complicated installation and higher cost make them impractical.

Other sensors utilize high Faraday-activity materials such as magnetic garnets. See, for example Rochford K. B., Rose A. H., Deeter M. N., Day G. W. "Faraday effect current sensor with improved sensitivity-bandwidth product." Optics Letters, vol. 19, (no. 22), November 1994, p. 1903 and Day G. W., Deeter M. N., Rose A. H.; Rochford K. B. "Faraday effect sensors for magnetic field and electric current." Proceedings of the SPIE—The International Society for Optical Engineering, vol. 2292, (Fiber Optic and Laser Sensors XII, San Diego, Calif., USA, 25–27 Jul. 1994.) 1994. p. 42. Such sensors generally exhibit high sensitivity and accuracy, but they can have limited dynamic range due to saturation of magnetic garnets and are also assembled optical components that can become misaligned or damaged with rough use. Another disadvantage is the relatively high temperature dependence of Faraday rotation in magnetic garnets. See e.g., Kamada O., Minemoto H., Itoh N., "Magnetooptical Properties Of $(BiGdY)_3Fe_5O_{12}$ For Optical Magnetic-field Sensors" Journal Of Applied Physics, 75: (10) 6801–6803, Part 2B May 1994.

The Faraday effect causes the polarization of linearly polarized light to rotate as it travels through a medium if a magnetic field is present parallel to the direction of propagation of the light. The magnitude of this rotation is different for different materials and in general is proportional to the strength of the applied magnetic field in the direction parallel to the propagation of the light, the length of propagation of the light through the material, and a characteristic of each material known as a Verdet constant (for paramagnetic materials such as, for example, glasses) or a Faraday constant (for ferromagnetic materials such as, for example, iron garnets). The change in the material properties due to the magnetic field is called circular birefringence. More specifically, when a material having a Verdet constant V is exposed to a magnetic field H and, due to this field, gains a magnetization projection onto the direction of the light propagation M, a linearly polarized light beam passing through the material along an optical path l has its polarization azimuth rotated by an amount $$\Phi_F = \int_l VM \cdot dl.$$

Either V or M, if constant over l, may be moved out of integral. In particular, if both V and M are constant over l, the equation set forth above simplifies to $\Phi_F = VM \cdot l$. By transmitting polarized light through the material, exposing the material to a magnetic field and measuring the change in polarization azimuth, one can determine the strength of the magnetic field in the direction of propagation of the light through the material. If an electrical current causes the field, the field and current directions are normal to each other. Optical sensors are also isolated and safe to use under high currents and voltages. The most frequently used are a method by Malus (see e.g., Rochford K. B.; Rose A. H.; Deeter M. N.; Day G. W. "Faraday effect current sensor with improved sensitivity-bandwidth product." Optics Letters, vol. 19, (no. 22), November 1994. p. 1903; Day G. W.; Deeter M. N.; Rose A. H.; Rochford K. B. "Faraday effect sensors for magnetic field and electric current", Proceedings of the SPIE—The International Society for Optical Engineering, vol. 2292, (Fiber Optic and Laser Sensors XII, San Diego, Calif., USA, 25 –27 Jul. 1994 p. 42) and a Sagnac interferometer method (see e.g., J. Blake et al. IEEE Transactions on Power Delivery, Vol. 11, No. 1 January 1996;

Moon Fuk Chan; Guansan Chen; Demokan M. S.; Hwa Yaw Tam "Optimal sensing of current based on an extrinsic Sagnac interferometer configuration", Optics and Lasers in Engineering, vol. 30, (no. 1), July 1998. p. 17). The former is simpler to build and less expensive, while the latter is generally more stable.

The Faraday effect is a non-reciprocal effect, which means that light passing through a material exhibiting this phenomenon will pick up an angle of rotation of polarization that is independent of the direction in which the light is traveling. Because of this non-reciprocity, multiple passes through the sensing element increase the magnitude of the polarization rotation and thereby enhance the sensitivity of the sensor proportionally. As an example, a current sensor using multiple passes is described by Ning, et al [Y. N. Ning et al in "Recent progress in optical current sensing techniques", *Review of Scientific Instruments* 66 (5), May 1995, pp. 3097–3111]. In this arrangement, a bulk glass exhibiting a high Faraday effect had a hole drilled through it to receive a wire carrying a current. Light was introduced into the bulk glass and reflected several times while going around the hole. The peculiar geometry of this detector limits its usefulness to detection of current flowing through a wire or to a narrow range of very similar uses. Another disadvantage was the necessity of breaking the power line during installation and the sensitivity of the sensor to mechanical noise because of the precise fiber-to-bulk glass alignment needed.

From another point of view, fiber and/or waveguide Bragg gratings have been known in the art for a long time as a sensor element for strain, temperature and pressure. Fiberoptic Bragg gratings (FBG) are known as periodic modulations of the refractive index in the core and/or cladding of an optical fiber, while waveguide Bragg gratings are usually introduced as a periodic variation in thickness and/or surface profile of one or more layers or thin films that the waveguide comprises. When the grating pitch of the Bragg grating coincides with half the wavelength of the light, the reflection conditions of the first order are satisfied.

If magneto-optical material is placed inside the optical resonator (Fabry-Perot [FP] cavity or multi-layer reflector stack, similar to narrow bandpass filter) the polarization rotation exhibits enhancement proportional to the squared quality of the resonator, which is defined by the reflectivity of the mirrors (or multi-layer reflectors). For instance, multilayer stacks of thin films, made like standard interference filters and air gaps between parallel mirrors are both manifestations of FP resonators, or etalons. A multilayer stack concept was demonstrated [Inoue et al. U.S. Pat. No. 6,262,949 Jul. 17, 2001] by fabricating alternating layers of $SiO_2$ and YIG by sputtering. Even though sputtered YIG is not as good a quality as LPE (Liquid-Phase Epitaxy)-grown YIG, the polarization rotation exhibited enhancement proportional to the squared quality factor of the resonator. (The quality factor is defined by the reflectivity of the mirrors and absorption of light in YIG). In another example, in this case a gas-filled gap between parallel mirrors, the magneto-optical activity of certain gases [Vallet M., Bretenaker F., Le Floch A., Le Naour R., Oger M. "The Malus Fabry-Perot interferometer," Optics Communications, vol. 168, (no.5–6), September 1999. p. 423] has been enhanced by 6 orders of magnitude with the use of such a resonator. This amplification of Faraday rotation can be explained in terms of the longer effective length that a photon travels though the resonator back and forth between mirrors before leaving the resonator. This means that by constructing the cavity with very high reflectivity mirrors, one can obtain an interaction length between the light and the 1 cm magneto-optical material on order equivalent to 10 km (and even more if said material is sufficiently transparent for these purposes).

The YIG/GGG (YIG layer serves as a waveguiding layer and GGG substrate serves as a waveguide substrate) waveguide realizations of such an approach for integrated optical isolators have been theoretically analyzed recently in [M. J. Steel et al., *J. of Lightwave Technology*, Vol. 18, No. 9, September 2000, pp. 1289, 1297]. Neither different birefringence effects, which are internal for such a waveguide design and are of importance, nor magnetic field and/or electrical current detection have been analyzed in these publications.

In fiber, one can construct high quality optical resonator structures more simply and cheaply than in volume optics or by any method mentioned in any reference so far. To do this, one can write a phase shifted Bragg grating into the fiber.

A preferred exemplary embodiment of the present invention makes use of these principles to provide a new fiber-optic magnetic field or electrical current sensor and associated system that can provide increases in accuracy, resolution and environmental stability. Briefly, the exemplary and illustrative design is based on a phase-shifted fiber or waveguide Bragg grating in which a Fabry-Perot resonator is formed around the phase shift. When the wavelength of incident light coincides with the wavelength of the Fabry-Perot resonator mode, the magnetic field induced polarization rotation of the waveguided light will be strongly enhanced.

In accordance with one non-limiting preferred exemplary aspect of a preferred illustrative embodiment of the invention, an apparatus for detecting a magnitude of a physical condition includes a light source, a magneto-optic Faraday effect sensing element comprising a fiber phase-shifted Bragg grating, first and second polarizers, and a detector. In this illustrative arrangement, the first polarizer is disposed between the light source and the magneto-optic Faraday effect sensing element, and the second polarizer (analyzer) is disposed in an optical path after the magneto-optic Faraday effect sensing element. The second polarizer detects the appearance of polarization state different from the one transmitted through the first polarizer. A detector optically coupled to the second polarizer responds to this detected polarization state.

In accordance with another non-limiting aspect, the light source may comprise a tunable laser such as, for example, a tunable VCSEL [C. J. Chang-Hasnain, *IEEE J. on Selected Topics in Quantum Electronics*, V. 6(6), November/December 2000; J. S. Harris, Jr., *IEEE J. on Selected Topics in Quantum Electronics*, V. 6(6), November/December 2000].

In accordance with yet another aspect, the light source may comprise a wideband light source, and the arrangement may comprise a circulator and fiber Bragg gratings or other wavelength filters such as for example Fabry-Perot filters whose filtering reflection feature coincides with the Bragg grating feature of the sensing element.

In accordance with yet another aspect, the light source may comprise a broadband light source such as for example a light emitting diode, a super luminescent diode or a lamp.

In accordance with yet another aspect, the detector may comprise a semiconductor photo diode, or a balanced photodetector. The balanced photodetector may comprise, for example, two photodiodes with a polarization splitter to detect opposite polarization components of the transmitted through the sensing element light.

In accordance with yet another non-limiting aspect, the physical condition being measured may comprise a magnetic field, a current flowing through an electrical conductor, or the like.

In accordance with yet another aspect, a phase-shifted fiber Bragg grating is written into the fiber. This fiber Bragg grating (which may be written into the fiber using ultraviolet laser radiation) may be written into a communication single-mode fiber with symmetrical core (low-birefringent) or a polarization-maintaining single-mode fiber with a highly asymmetric core (high-birefringent).

In accordance with yet another non-limiting aspect, the phase-shifted fiber Bragg grating may comprise a constant-period Bragg grating, or it could be constructed from two or more superimposed phase-shifted Bragg gratings to compensate the birefringence.

In accordance with yet another aspect, the phase-shifted fiber Bragg grating incorporates at least one phase shift.

In accordance with yet another aspect, the exemplary sensing arrangement may include an environmental effects compensation feedback arrangement together with a tunable laser such as, for example, a tunable VCSEL.

In accordance with yet another aspect, the magneto-optic Faraday effect sensing element may include flux concentrators that increase the value of the magnetic field at the position of the phase shift(s).

In accordance with yet another aspect, a waveguide may be included that is constructed so the waveguide mode is at least partially localized in the magneto-optically active material. The magneto-optically active material may, for example, have an in-plane magnetization anisotropy. Another hard magnetic material layer may be disposed such that the in-plane hard axis of the hard magnetic material layer lies in the plane of incidence of light and is collinear to an external magnetic field to be measured. A hard magnetic material layer may produce uniform bias magnetic field in the plane of the Faraday-active magnetic material.

In accordance with another aspect of a non-limiting illustrative embodiment, a hard magnet is placed in the vicinity of the sensing element such that the magnetic field produced by the hard magnet is uniform in the Faraday-active magnetic material and lies in the plane of the Faraday-active material. In accordance with this aspect, the direction of the magnetic field produced by at least one hard magnet is perpendicular to an external magnetic field to be measured. The hard magnet thus provides a uniform bias magnetic field in the plane of the Faraday-active magnetic material.

In accordance with yet another aspect of a non-limiting illustrative arrangement, the Faraday-active magnetic material may comprise a magnetic garnet single crystal thin film. Alternatively, the Faraday-active magnetic material may be constructed from two or more layers of magnetic garnet single crystal thin films with different compositions and magneto-optical properties. The Faraday-active magnetic material may be any other transparent material with Faraday activity sufficiently high for its purpose.

The following are additional advantageous features and advantages provided by the non-limiting illustrative exemplary embodiments:

Phase shifted fiber Bragg grating magnetic field or current sensor.
Multiple phase-shifted fiber Bragg grating magnetic field or current sensor.
Superimposed phase-shifted fiber Bragg grating magnetic field or current sensor.
Phase shifted waveguide Bragg grating magnetic field or current sensor.
Multiple phase-shifted waveguide Bragg grating magnetic field or current sensor.
Superimposed phase-shifted waveguide Bragg grating magnetic field or current sensor (the important design for birefringence compensation).
Tunable VCSEL based read-out method.
Circulator+number of optical filter based read-out scheme.

BRIEF DESCRIPTION OF THE DRAWINGS

These and other features and advantages provided in accordance with exemplary and illustrative embodiments of the present invention may be better and more completely understood by referring to the following detailed description in conjunction with drawings, of which:

FIG. 3a shows an exemplary plot of numerically calculated polarization rotation (Faraday effect) spectra of the magneto-optic sensing elements at the applied 1 kOe magnetic field directed along the axis of the fiber wherein the magneto-optic sensing elements are Bragg gratings with 0.25, 0.5 and 1 cm length, and all other parameters as in FIG. 2a;

FIG. 3b shows an exemplary plot of numerically calculated polarization rotation (Faraday effect) spectra of the magneto-optic sensing elements at the applied 1 kOe magnetic field directed along the axis of the fiber wherein the magneto-optic sensing elements are Bragg gratings with refractive index contrast between the exposed and unexposed areas of $\Delta n = 10^{-3}$, $5*10^{-4}$ and $2*10^{-4}$, and all other parameters as in FIG. 2a;

FIG. 8 shows an exemplary preferred embodiment of an overall sensing system;

FIG. 8A shows an example detector including first and second photodetectors and a polarizing beam splitter;

FIG. 9 shows an exemplary transmissivity spectrum plot;

DETAILED DESCRIPTION OF PRESENTLY PREFERRED EXAMPLE EMBODIMENTS

Figure 1A:
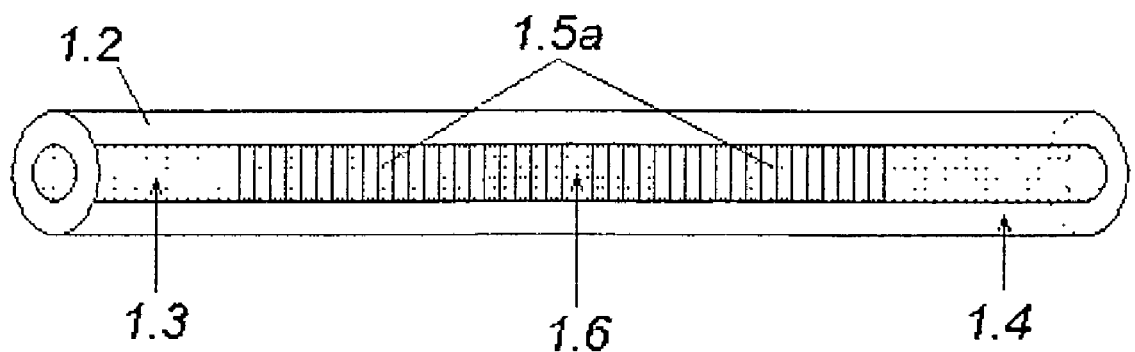
FIGS. 1A, 1B and 1C show example non-limiting illustrative fiber magneto-optic sensing elements.
Figure 1B:
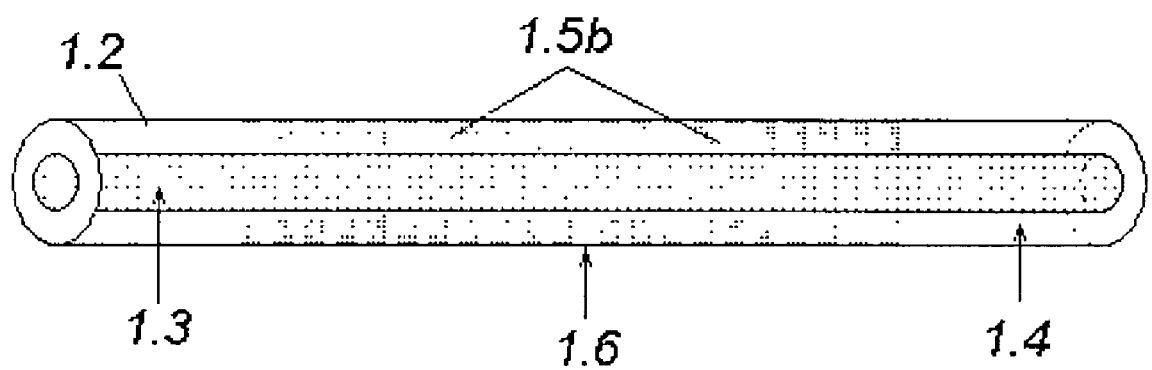
Figure 1C:
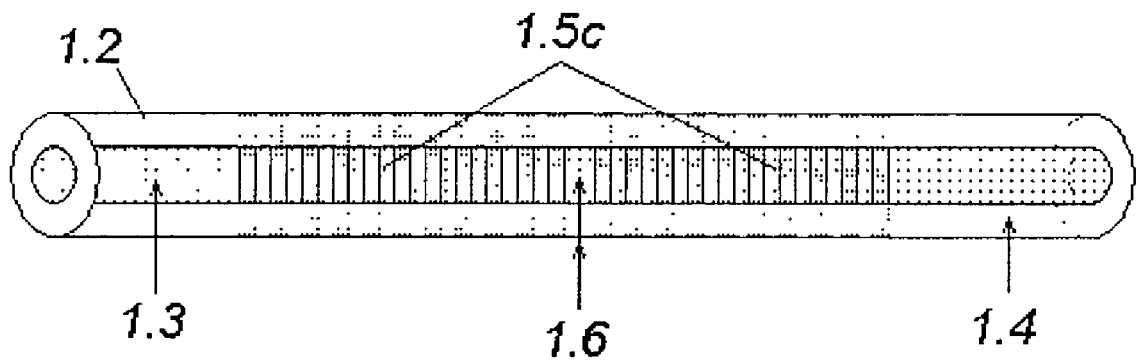

FIG. 1 shows an exemplary illustrative magneto-optic sensing element in accordance with a non-limiting aspect of a preferred embodiment of the present invention. Referring now to FIG. 1, a magneto-optic sensing element 1.1 is provided by the fiber 1.2 having core 1.3 and cladding 1.4 and having Bragg grating 1.5 written into core 1.5a, cladding 1.5b or both 1.5c by UV laser exposure through a phase mask or any technique well known to those of ordinary skill in the art. The exposed areas of fiber core, cladding, or core and cladding (depending on type of fiber and exposure method) exhibit small changes in refractive index. Although usually the change in refractive index is quite small, the number of such regions can be huge (10000 or more), so the reflectivity level can be very high (up to 0.99999), leading to the possibility of forming high quality FP (Fabry-Perot) resonators. FP resonators will be formed if a Bragg grating 1.5 has at least one phase shift 1.6, equal to integer multiple of π.

Figure 2A:
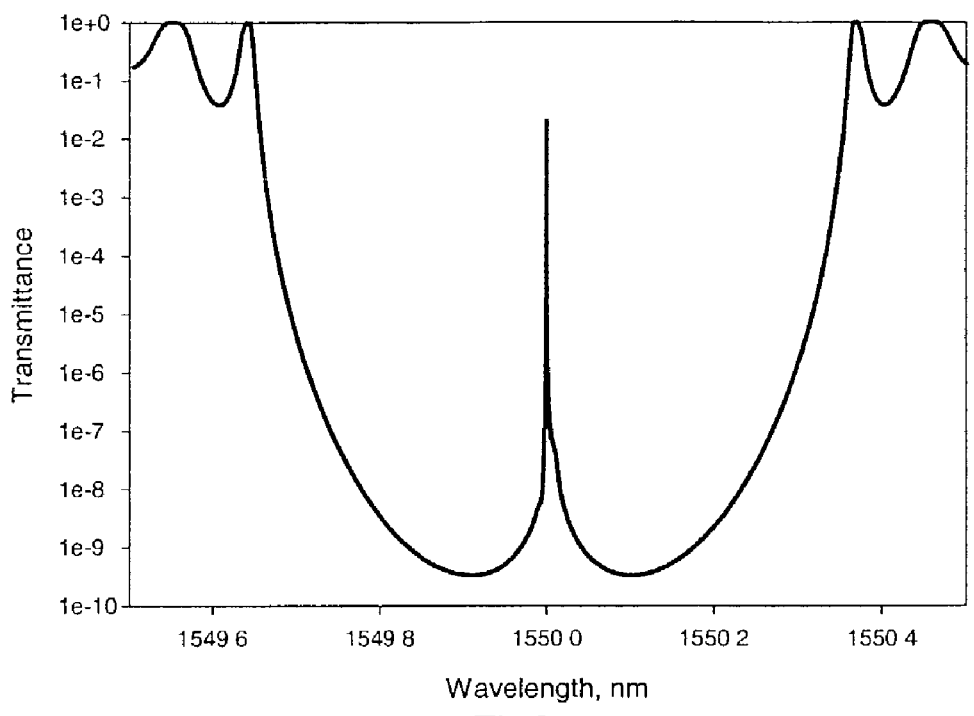
FIG. 2a shows an exemplary plot of numerically calculated transmission spectrum of the magneto-optic sensing element at the polarization of incident light wherein the magneto-optic sensing element is a 1 cm long FBG with refractive index contrast between the ultraviolet-exposed and unexposed areas of $\Delta n = 10^{-3}$ having single phase shift exactly in the middle of the FBG.
Figure 2B:
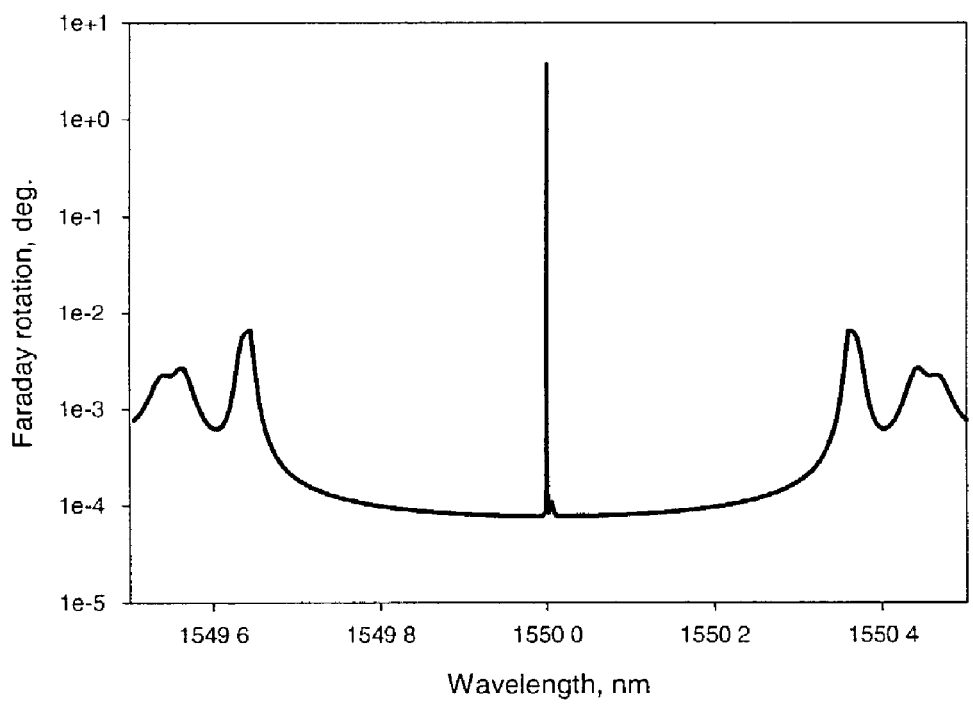
FIG. 2b shows an exemplary plot of numerically calculated polarization rotation (Faraday effect) spectrum of the magneto-optic sensing element of FIG. 2a at the 1 kOe applied magnetic field directed along the axis of the fiber.

Since the fiber core shows some small magnetic field-induced polarization rotation, the light traveling through the fiber Bragg grating also will exhibit polarization rotation, proportional to the effective length that it travels while passing through the Bragg grating. Since in the phase-shifted fiber Bragg grating at the wavelength of the phase shift transmission maximum (FP resonator frequency), light travels a distance that considerably exceeds the physical Bragg grating length, the polarization rotation at this wavelength will also be increased by the square of the FP resonator quality. FIG. 2a shows an exemplary illustrative numerically calculated spectrum of a transmission through the magneto-optic sensing element at the polarization of incident light, and FIG. 2b shows an exemplary numerically calculated spectrum of the polarization rotation (Faraday effect) of magneto optic sensing element. The magneto-optic sensing element assumed for FIGS. 2a and 2b was 1 cm long FBG (fiber Bragg grating) with refractive index contrast between the exposed and unexposed areas of $\Delta n=10^{-3}$ having a single phase shift exactly in the middle of the FBG. The fiber was assumed to be single-mode with circular core. Optical absorption, scattering and birefringence have not been taken into account in these calculations. For polarization rotation calculations, the Verdet constant of the fiber was assumed to be V=1 deg/(T*m). In FIG. 2b, the polarization rotation is calculated for 1 kOe magnetic field, applied parallel to the axis of the fiber.

Figure 3A:
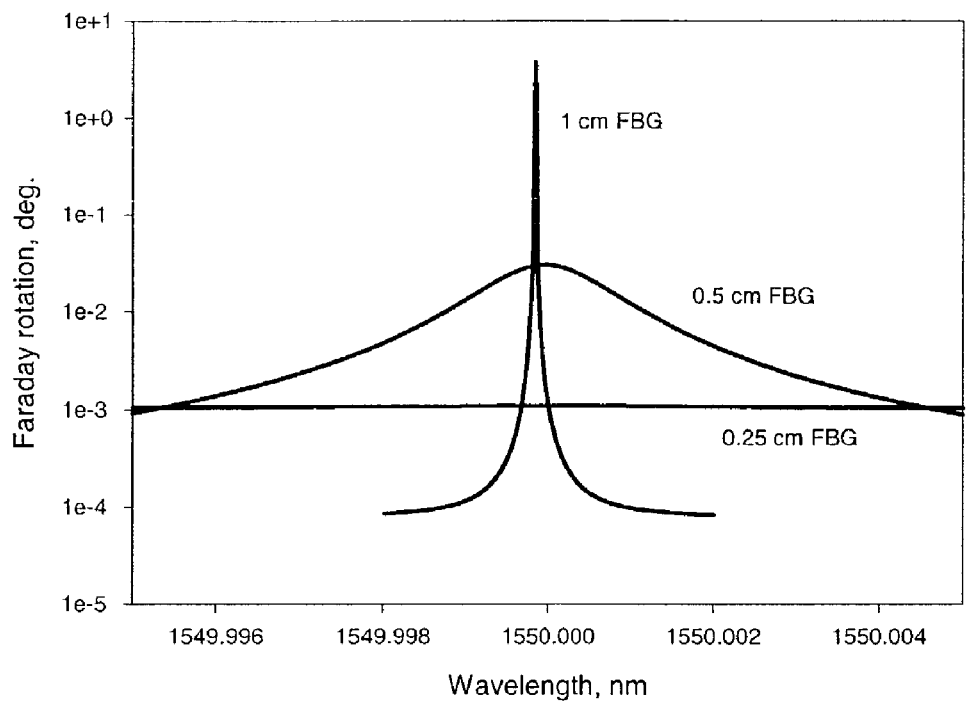
Figure 3B:
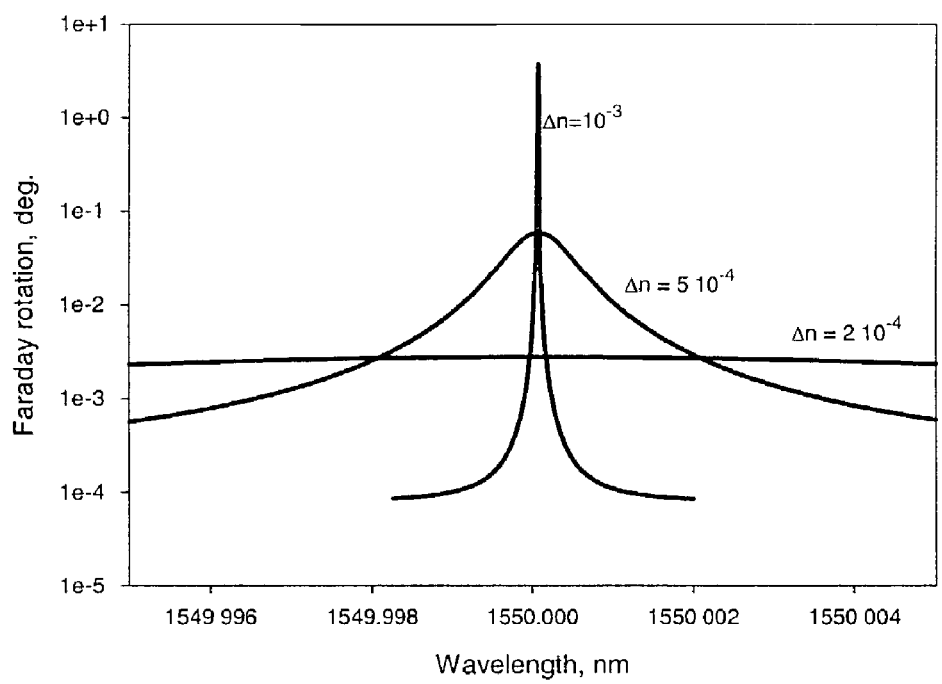

As follows from FIG. 2b, for such an exemplary structure the polarization rotation enhancement factor approaches four orders of magnitude at its peak value. As mentioned above, the enhancement factor is a function of the quality of the resonator in the form of two reflective parts of the FBG around the phase shift. Hence, for the single-phase-shifted FBG the Faraday effect enhancement is closely connected to the spectral width of the phase-shift resonance. As an illustration, FIG. 3a gives illustrative numerically calculated spectral dependences of the polarization rotation of fiber Bragg gratings with 0.25, 0.5 and 1 cm length, and all other parameters as in FIG. 2b. It follows from FIG. 3a that the shorter the FBG, the lower the Faraday effect enhancement, and the wider the wavelength band where the enhancement take place. The same is true when the length of FBG is set constant while the refractive index contrast between the exposed and unexposed areas (i.e., the strength of the FBG) is decreasing. As an illustration of this statement, FIG. 3b shows the numerically calculated spectral dependences of the polarization rotation of fiber Bragg gratings with refractive index contrast between the exposed and unexposed areas of $\Delta n=10^{-3}$, $5*10^{-4}$ and $2*10^{-4}$, and all other parameters as in FIG. 2b.

The exemplary design disclosed herein has some similarity to the enhancements in a multi-layer stack having a magneto-optical layer (or layers) in it, although in the fiber case there are some differences. In the volume optic case at normal incidence, there is no difference in refractive index (and through that in propagation constant) between any polarizations of incident light (due to axial symmetry), and magnetic field-induced circular birefringence induces two modes of right-hand and left-hand circular polarization. In communication (circular core) fiber, axial symmetry also takes place. However, the communication fiber never has a perfectly circular core—there is always some shape-induced birefringence. Said small perturbation in fiber symmetry leads to a Faraday rotation limiting effect, which can cause a decrease in the Faraday rotation and limits, through that, the detection limit of the sensor. For communication fiber, this effect is usually small, while for PM (polarization-maintaining) fiber with a highly asymmetric core it can play more important role. While in the multi-turn fiber current sensor (prior art, see for example [Rose A. H. "Playing with fire and fibers", IEEE Circuits and Devices Magazine, vol. 15, (no. 5), IEEE, September 1999. p. 41]) said effect not very important due to the small overall Faraday rotation, in the presented fiber-optic magnetic field and/or current sensor design this effect can be enhanced due to the utilization of a Bragg grating, which reflects light of different polarizations at different wavelengths. The effect of shape-induced birefringence could be significant for highly birefringent PM fibers—the enhancement could be completely suppressed. An illustrative way to overcome such an effect will be disclosed later.

Another effect, which could limit sensitivity and accuracy of the presented sensor, is the small but finite birefringence of fiber core and cladding materials. This effect, together with stress-induced birefringence, limits resolution of multi-turn fiber current sensors. Although stress-induced birefringence in the sensor will be strongly suppressed due to higher magnetic field-induced polarization rotation per unit fiber length, the effect still will be present to some extent. The third limiting effect is the small but finite absorption of light in the fiber (finesse of FP resonator is limited by losses in it).

The following simple estimate shows that one could easily neglect absorption in the fiber: Assuming typical losses in fiber in the range of 0.1 dB/km, and both Bragg grating branches on either side of the phase shift having reflectivity 0.999, the effective traveling length of the light with the wavelength, corresponding to the FP resonator eigen frequency will exceed 2 km. This value is more than enough to produce the polarization rotation needed for sensing purposes.

The way to overcome first limiting factor—shape induced birefringence—is more difficult. The approach disclosed here will suppress the stress-induced birefringence not only in the highly birefringent fiber, but also in a planar rib waveguides, where birefringence sometimes exceeds by far that of the fiber (up to 3 orders of magnitude). The principle of compensation is novel: Instead of the constant period fiber Bragg grating, a "superimposed" Bragg grating can be utilized.

Figure 4A:
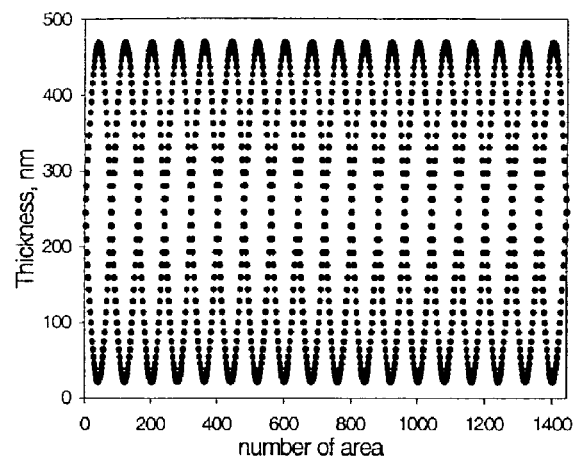
FIGS. 4a, 4b, 4c show plots of exemplary thicknesses of exposed and unexposed layers.
Figure 4B:
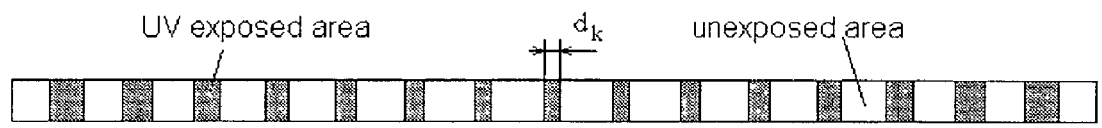
Figure 4C:
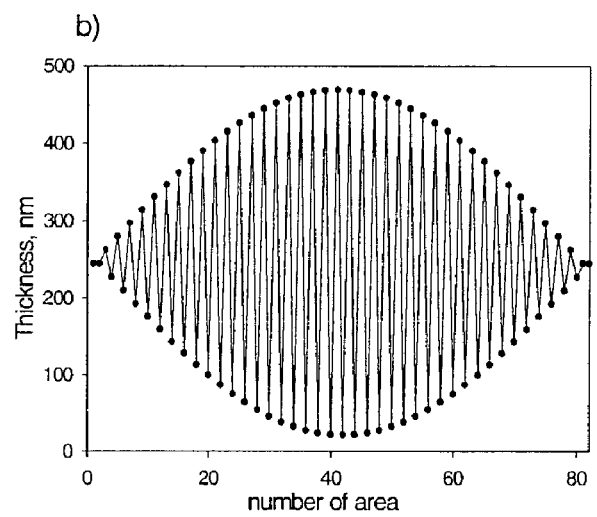
Figure 5:
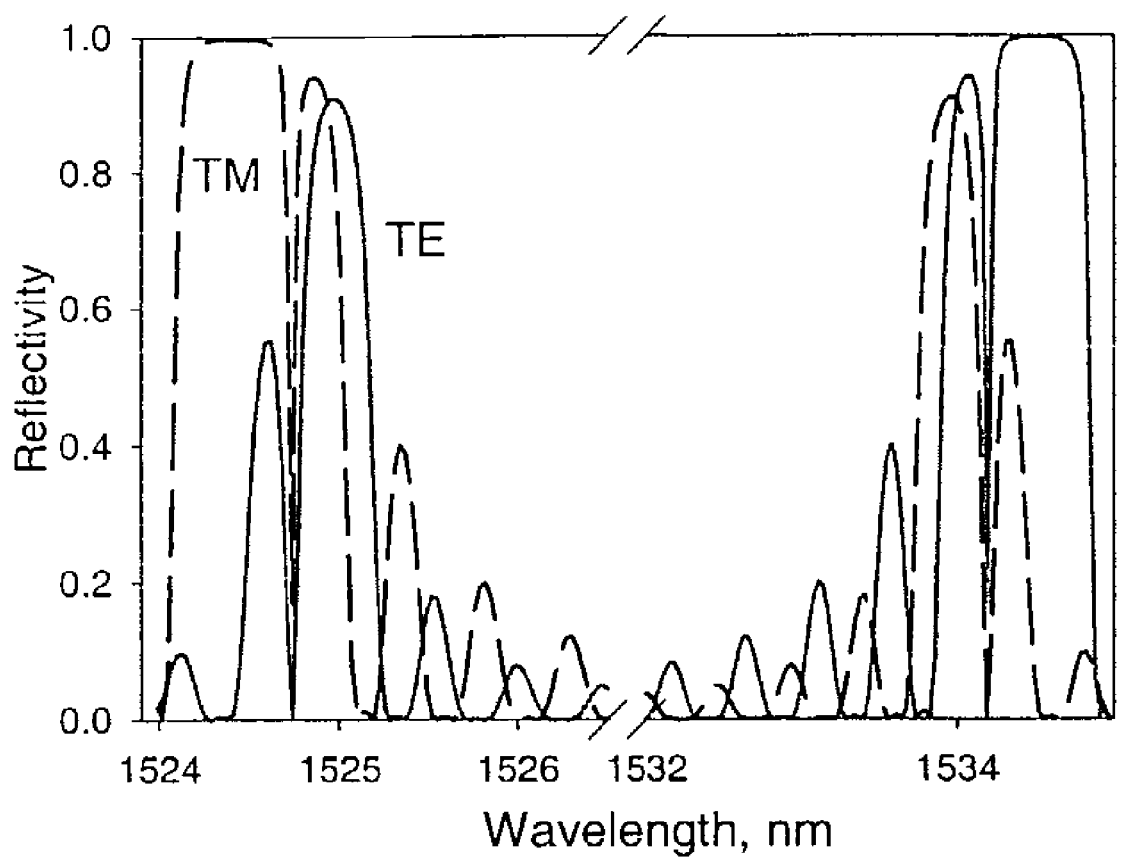
FIG. 5 shows an exemplary reflection spectrum plot.

A superimposed Bragg grating can be imagined as a superposition of two or more constant period Bragg gratings on the same area of fiber or waveguide. As mentioned above, in highly birefringent fibers and in planar waveguides, the propagation constants of TE and TM modes are separated, as are the wavelengths of the corresponding Bragg reflection peaks. While the first of the superimposed, phase-shifted Bragg gratings provides the FP cavity, the second of them provides matching (or coupling) between the TE and TM modes. FIGS. 4a, 4c are exemplary plots of the thickness of exposed ($d_{2k}$) and unexposed layers ($d_{2k+1}$) as a function of layer number (k) in the superimposed highly-birefringent fiber Bragg grating, and FIG. 4b is an illustrative drawing of a section of superimposed fiber Bragg grating. The thickness of the exposed and unexposed sections in such a superimposed grating is given in FIG. 4a (fine resolution) and FIG. 4c (coarse resolution) as a function of section number while a sketch of the corresponding exposed sections in the fiber is given in FIG. 4b. The reflection spectra of both polarizations of such a grating in the YIG waveguide structure (explained in more detail later) are given in FIG. 5—which shows an exemplary numerically calculated reflection spectrum of superimposed phase-shifted Bragg grating on YIG waveguide chip. $R_{TE}$—reflection of TE mode, $R_{TM}$—reflection of TM mode.

Fabrication of such a structure using a phase-mask method of UV laser exposure is straightforward.

As follows from FIGS. 2–3, for the FBG having a single phase shift, a tradeoff exists between the enhancement factor and resonance spectral width. As mentioned above, the enhancement factor is a function of the quality of the FP resonance, but so is the resonance spectral width. For example, the predicted four order enhancement peak in FIG. 2b has only 0.2 pm spectral width, which is impractical for many or most applications, since it is narrower than most of the laser diode spectra not to mention noise caused by environmental variations of the peak spectral position.

Figure 6A:
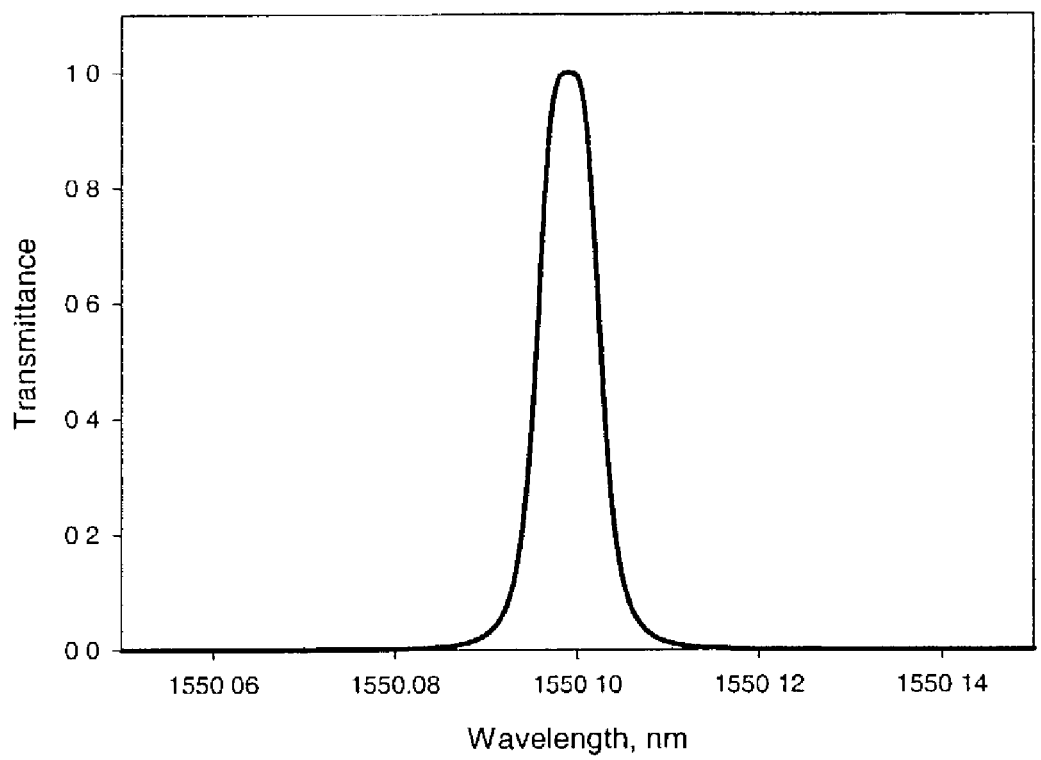
FIG. 6a shows an exemplary plot of numerically calculated transmission spectrum of the magneto-optic sensing element in the form of 1 cm long FBG with refractive index contrast between the exposed and unexposed areas of $\Delta n = 10^{-3}$ having seven phase shifts.
Figure 6B:
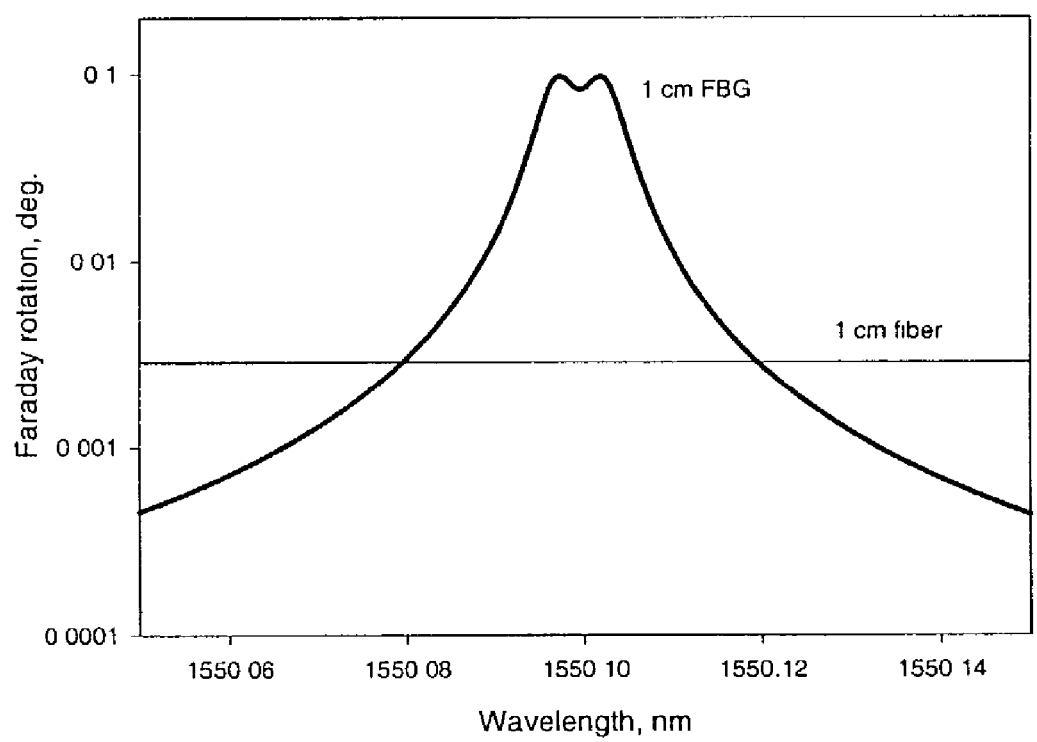
FIG. 6b shows an exemplary plot of numerically calculated polarization rotation (Faraday effect) spectrum of the magneto-optic sensing element of FIG. 6a at the 1 kOe applied magnetic field directed along the axis of the fiber.

One exemplary way to overcome the enhancement factor/resonance spectral width difficulty is to use a the multiple-phase-shifted FBG. FIG. 6a shows the transmission spectrum of an exemplary FBG having the structure {(UE)$^{5000}$U(UE)$^{5000}$UU(UE)$^{5000}$U(UE)$^{5000}$UU(UE)$^{5000}$ U(UE)$^{5000}$ UU(UE)$^{5000}$U(UE)$^{5000}$}, where U denotes the unexposed section of fiber while E denotes exposed section of fiber. The refractive index contrast between the exposed and unexposed areas is assumed to be $\Delta n=10^{-3}$. FIG. 6b shows exemplary polarization rotation (Faraday effect) spectrum of the FBG of FIG. 6a with a 1 kOe applied magnetic field directed along the axis of the fiber (the Verdet constant of the fiber core was assumed to be 1 deg/(T*m)). As follows from FIG. 6b, the one and a half order enhancement of the Faraday effect takes place over 10 pm spectral range (contrary to less that 1.5 pm of the same enhancement for single-phase-shifted FBG in FIGS. 3a and 3b). Hence, multiple-phase shift can substantially decrease the enhancement factor/resonance spectral width constraint.

Figure 7A:
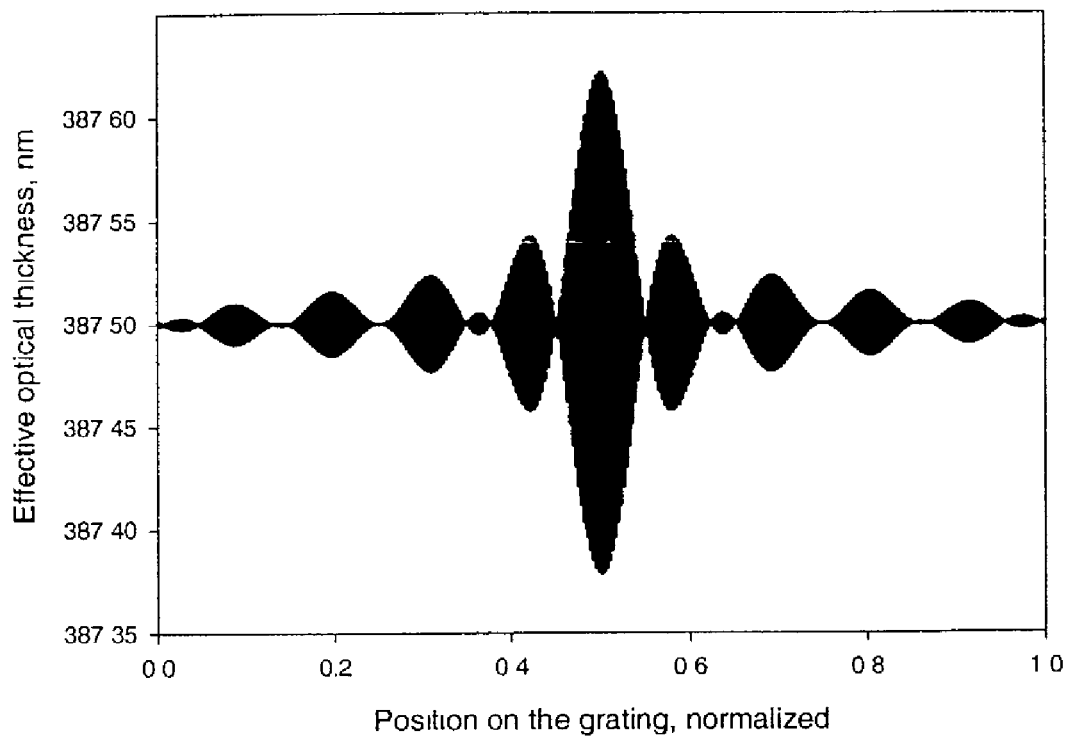
FIGS. 7a and 7b show exemplary plots of the optical thickness of the apodized FBG sections as a function of section number in coarse and fine resolution, respectively.
Figure 7B:
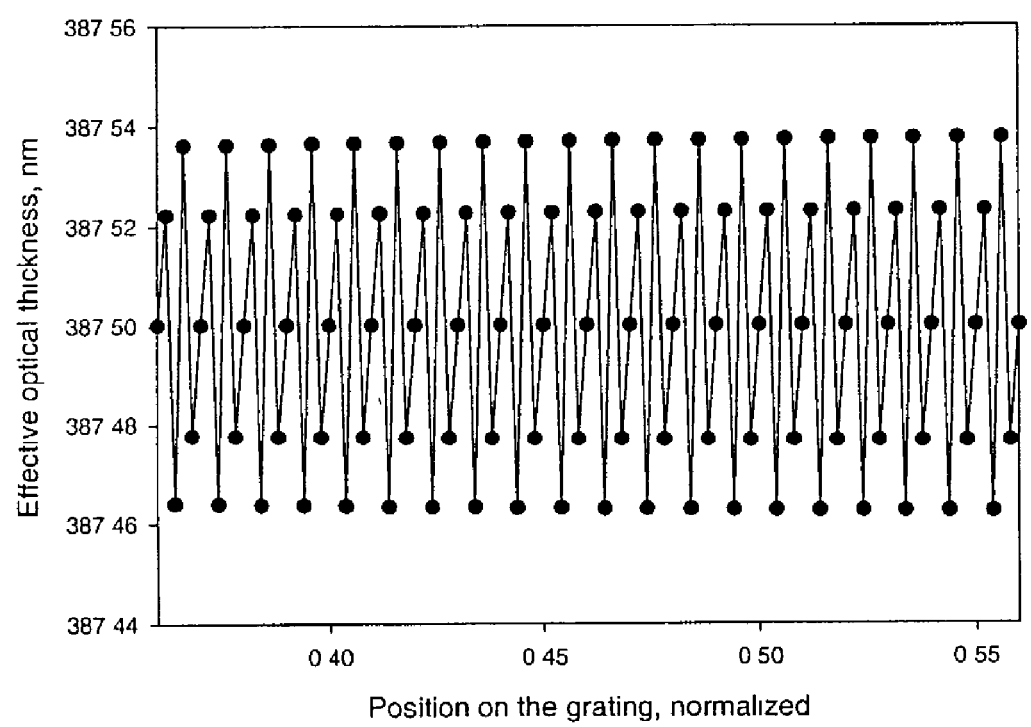
Figure 7C:
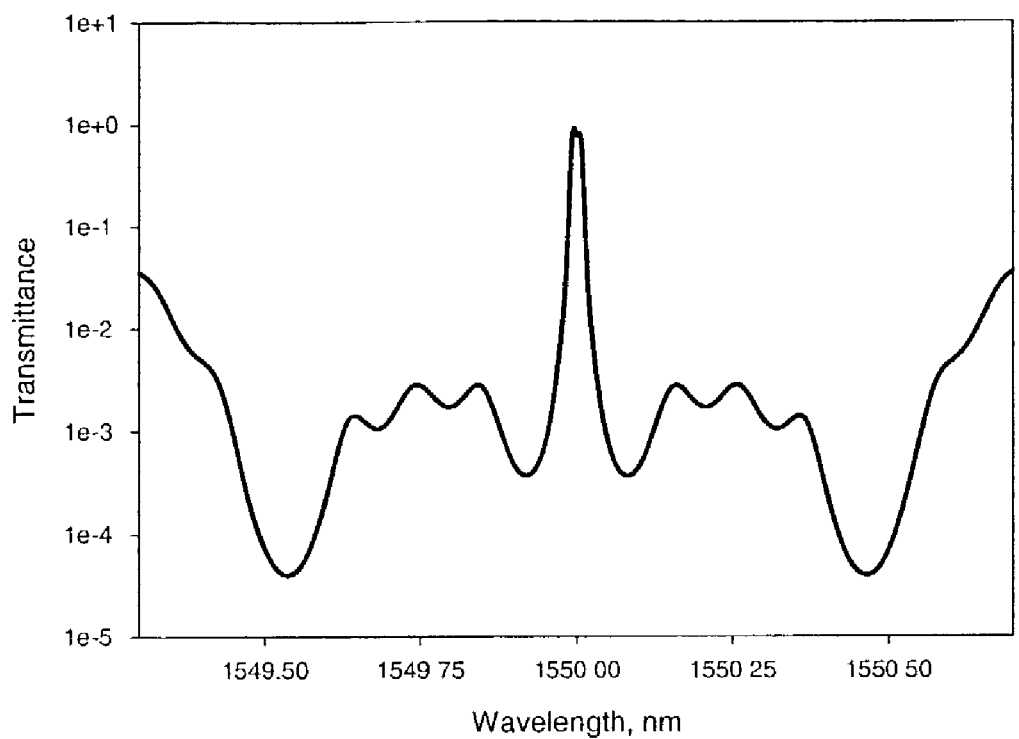
FIG. 7c shows an exemplary plot of numerically calculated transmission spectrum of the magneto-optic sensing element in the form of 1 cm long FBG of FIGS. 7a and 7b.
Figure 7D:
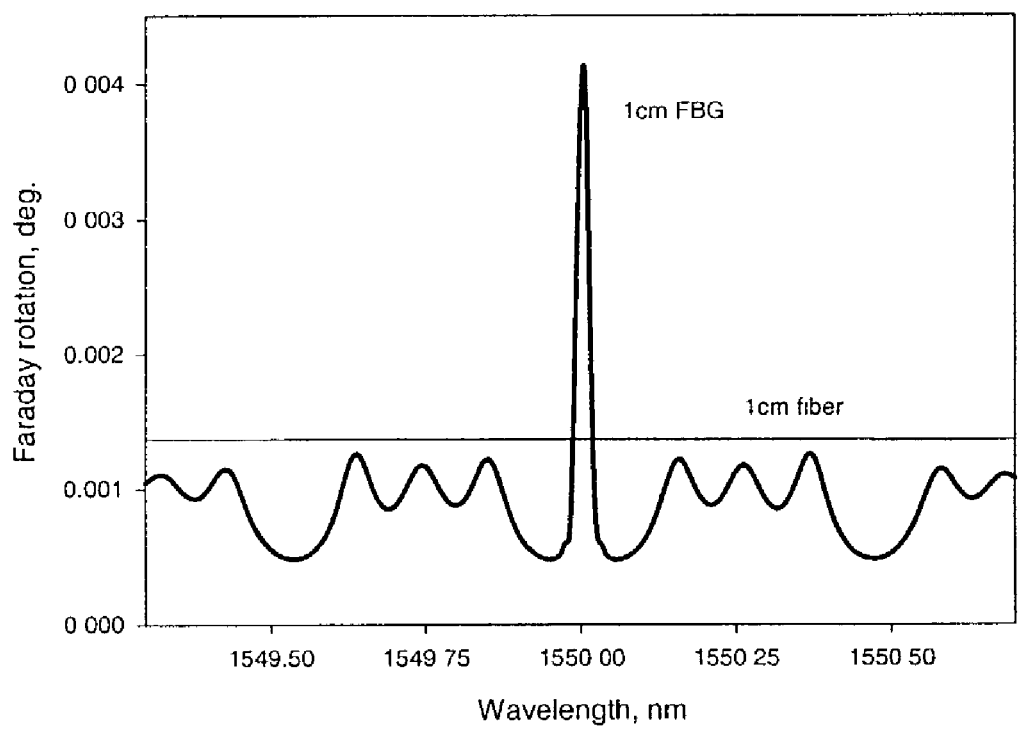
FIG. 7d shows an exemplary plot of numerically calculated polarization rotation (Faraday effect) spectrum of the magneto-optic sensing element of FIGS. 7a and 7b at the 1 kOe applied magnetic field directed along the axis of the fiber.

Another solution of the enhancement factor/resonance spectral width tradeoff problem is to use an apodized FBG structure. As an example, the optical thickness (which is a product of the average effective refractive index of the section and the section thickness) of the exposed and unexposed sections in such a superimposed grating is given in FIG. 7a (coarse resolution) and FIG. 7b (fine resolution) as a function of section number. Such a FBG can be inscribed, for example, through a combination of two masks—one phase mask similar to the one that used for uniform FBG inscriptions and a second absorption mask to modulate the illumination intensity on a larger scale. Exemplary transmittance spectrum of the FBG of FIGS. 7a and 7b is shown in FIG. 7c, while the polarization rotation (Faraday effect) spectrum of the same FBG is shown in FIG. 7d for the magnetic field of 1 kOe, applied parallel to the fiber axis.

The fiber realization of such a sensor will give at least an order more magnetic field or electrical current resolution with respect to competitive technologies. The dynamic range of the disclosed current sensor is in the range of 10 mA to 20 kA. This is one order of magnitude improvement in sensitivity, dynamic range, and resolution, with respect to prior art fiber-based sensors together with more compact, non-wrap-around sensor.

The preferred exemplary embodiment herein thus performs sensing in a tiny wavelength span (4–10 pm) within the phase shift-induced transmission peak (see FIG. 2). The operating wavelength of the disclosed sensor will vary with temperature, pressure or strain, so the use of constant-wavelength light source (such as a laser) is disadvantageous. This means that in order to get an environmentally stable sensor, wavelength tuning according to the perturbations is desired. Tunable lasers are ideally suited for such an application. External-cavity type tunable lasers are expensive, although they provide continuous tuning across a quite wide wavelength band (for example from 1500 to 1650 nm), and thus can be utilized for the multiple sensor readout through wavelength division multiplexing (WDM). For the single-sensor instruments, however, such lasers are generally not cost effective. Some promising low-cost tunable lasers have been suggested recently. Said lasers include tunable fiber laser, tunable DBR laser and tunable VCSELs. All of these designs are suitable for such applications. Recently developed tunable VCSELs (Vertical Cavity Surface Emitting Laser) will probably be best suited for such applications since they promise both the lowest cost among other designs and fast tuning speed, which will be required if the environment is changing.

FIG. 8 is a schematic block diagram of an exemplary illustrative embodiment of a fiber-optic magnetic field or current sensor and overall sensing system or instrument 100. The fiber-optic magnetic field or current sensor and instrument 100 of FIG. 8 are based on tunable laser as a tunable narrowband light source. A tunable VCSEL 102 (it should be noted that any other tunable laser known to those skilled in the art can be employed instead) provides wavelength-tunable light to the optical fiber 104. An optical circulator 106 is disposed to prevent the reflected light from the Bragg grating 108 from affecting the tunable VCSEL performance, and to prevent the light of the tunable VCSEL from directly illuminating the first photodiode 110 and to direct light reflected from the Bragg grating sensor to the first photodiode. A fiber-optic polarizer 112 defines the polarization of the light incident on the Bragg grating 108, while the analyzer is oriented to maximize the effect of the imposed magnetic field on the transmitted intensity. An exit optical fiber 114 is provided to couple the optical output transmitted through the analyzer to the second photodetector 116, the electrical signal 118 from which is directed to the control block circuitry (processor) 120 and the external electronic circuitry as required.

The illustrative instrument 100 is operated in a feedback loop: The wavelength position of the phase shift-induced Faraday rotation maximum in transmission mode of Bragg grating sensor (FIG. 4) coincides with the wavelength position of the phase shift-induced transmission peak of the same Bragg grating sensor (FIG. 9). FIG. 9 is an exemplary plot of a transmission spectrum of the magneto-optic sensing element together with the spectrum of the light suitable for operation of sensing element in the instrument, based on broadband light source and wavelength filters. The wavelength of the tunable VCSEL will be continuously tuned to keep the signal from the first photodiode at minimum position—known as a null-balanced scheme. All parameters can be actively changed, adjusted and recalibrated by the instrument processor. Using such a scheme, it is possible to suppress the environmental effects like pressure, temperature or strain, if these effects are changing slowly.

While the tunable laser is probably the best solution to interrogate a single sensor, it is not the only possible realization of the instrument. Wide wavelength sources like LED's or SLED's (Superluminescent Light-Emitting Diode) could be used in the scheme described below.

Figure 10:
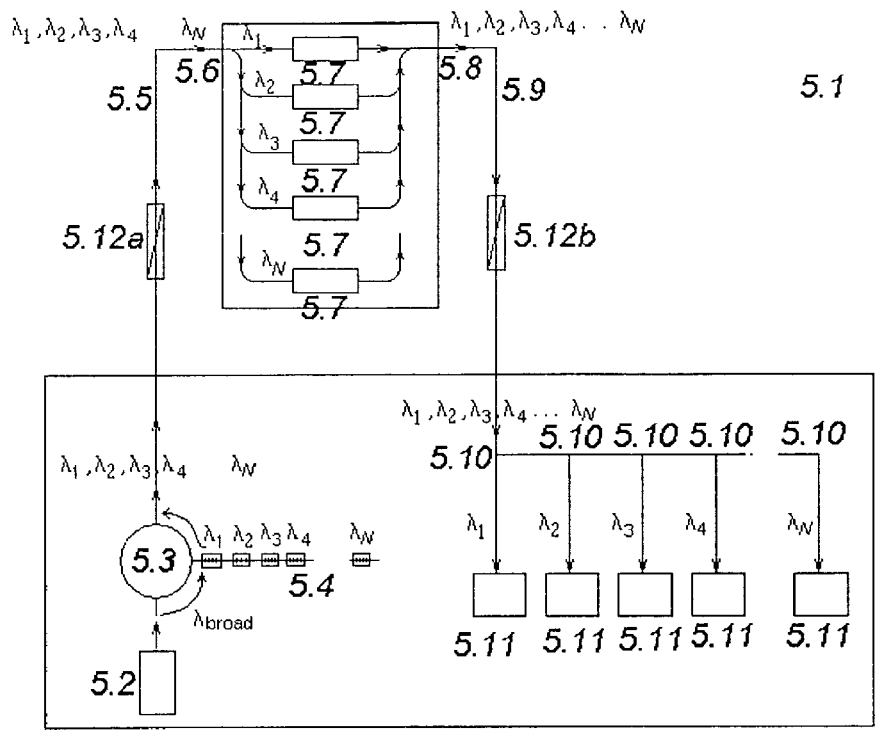
FIG. 10 is a schematic diagram of an illustrative magneto-optic sensing system, based on broadband light source and wavelength filters, with a plurality of sensing elements.

Referring now to FIG. 10, an illustrative magneto-optic sensing system 5.1 includes a light source 5.2 that may be provided, for example, as an LED operating at communication wavelengths around 1300 nm or 1550 nm, a superluminescent diode with similar arrangement, or any other broadband light source well known to those of ordinary skill in the art. The light source 5.2 emits light, which is coupled into the fiber and travels through the fiber towards the circulator 5.3, which directs light to the Bragg grating array 5.4. The periods of gratings inside array 5.4 should coincide with the periods of the phase shifted Bragg gratings in the array 5.7, as specified below.

The light reflected at specified wavelength bands (set by the grating array 5.3) is returned back to the circulator and directed towards the fiber 5.5, which leads light to the first polarizer 5.13, disposed to transmit the first polarization state and to block the second polarization state. After the polarizer, the light travels to the array of sensing elements 5.7. Said array divides the light through a WDM polarization preserving divider 5.6 into a set of optical paths, which lead the light to an array of sensing elements 5.7 having phase-shifted Bragg gratings. After the grating array 5.7, the light, now having an altered state of polarization at each wavelength determined by the value of the magnetic field (or electrical current) at the sensing element corresponding to said wavelength, is combined by a WDM polarization preserving combiner (coupler) 5.8 and sent through the fiber 5.9 to the second polarizer 5.14b adapted to attenuate the intensity of light having the first polarization characteristic.

Light that is transmitted through the set of sensing elements 5.7 may have a rotation of polarization relative to the incident light. This rotation of polarization effectively converts a fraction of one polarization to the other. Thus, the light having intensity, phase and polarization provided by the first polarizer 5.14a, the set of sensing elements 5.7, and the second polarizer 5.14b, is transmitted through the fiber 5.9 to a WDM element 5.10 which divides the light into the set of optical paths according to the wavelength which coincides with the wavelength set into the grating array 5.4 and sensing elements array 5.7, which directs the set of light bands to the array of photodetectors 5.11.

Each detector from detector array 5.11 may be provided as a semiconductor diode, a photomultiplier tube or as any other type of optical detector well known to those of ordinary skill in the art. Thus multiplexing of many sensors can be realized.

Figure 11:
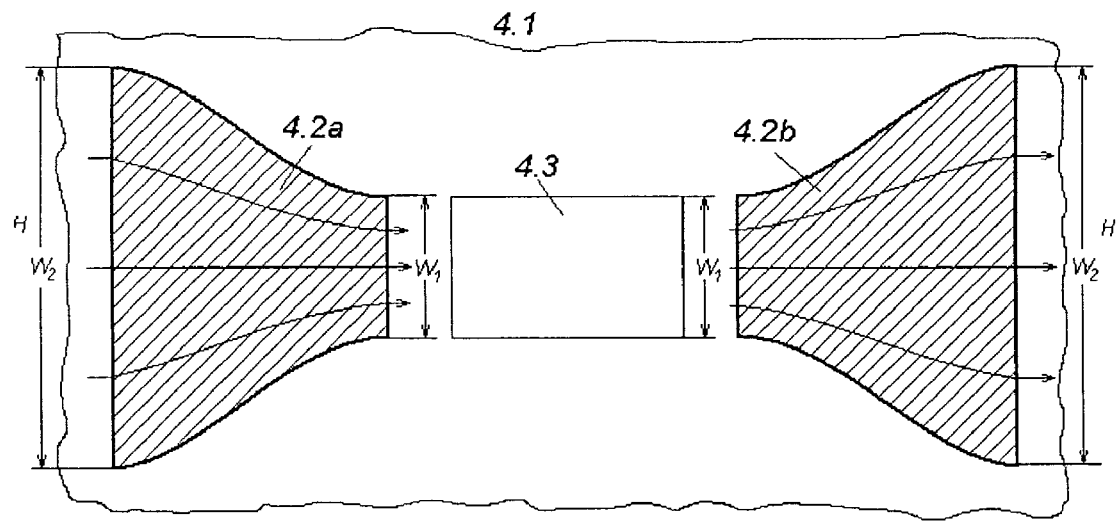
FIG. 11 shows an illustrative sensor including a flux concentrator disposed about a sensing element.

Referring now to FIG. 11, an illustrative sensor element 4.1 includes a flux concentrator having portions 4.2a and 4.2b (generally denoted 4.2) disposed about a magnetic field (or electrical current) sensing element 4.3. The flux concentrator 4.2 is preferably provided from a multidomain, high relative magnetic permeability material (greater than 1000).

The flux concentrator 4.2 is provided having such a shape so the magnetic flux lines around the flux concentrator 4.2 are directed through the flux concentrator 4.2. Furthermore, the shape of the flux concentrator 4.2 may be selected such as the concentrated magnetic field flux lines emerge from the flux concentrator 4.2 providing the sensor 4.3 immersed in an enhanced, uniform magnetic field. The flux concentrator 4.2 may be planar or three-dimensional and may be provided by a film deposition technique, machining or any other technique well known to those of ordinary skill of the art. The particular shape of the flux concentrator 4.2 may depend on the particular application, and may be determined by well-known magnetostatic calculation techniques. The net enhancement in the magnetic field relative to the ambient magnetic field at the location of the sensor 4.3 is generally dependent on the size and shape of the flux concentrator 4.2 and the permeability and other magnetic parameters of the constituent elements or alloys.

The flux concentrator 4.2 may be advantageous in magneto-optic magnetic field sensor applications requiring a high degree of sensitivity. In such applications the flux concentrator 4.2 may be provided from a high permeability film such as iron. In this case, the presence of the flux concentrator 4.2 increases the sensitivity of a system by increasing the total magnetic field value relative to the ambient magnetic field environment at the location of the sensing element.

The flux concentrator 4.2 is here provided having a generally triangular (or conical in three-dimensional case) shape with curved side edges as shown. The flux concentrator portions 4.2a, 4.2b may be provided having lengths $L_1$, $L_4$ typically in the range of about 1 millimeter (mm) to 50 mm. The lengths $L_1$ and $L_4$ need not be equal. Each of the flux concentrator portions 4.2a, 4.2b are spaced from the sensor element 4.3 by distances $L_2$ and $L_3$ typically in the range of about 0.01 mm to 2 mm. A particular selection of distances $L_1$–$L_4$ may be made based upon a variety of factors including but not limited to the characteristics of the material from which the flux concentrator 4.2 and the sensor element 4.3, are made. For example the thickness and permeability characteristics of the material are two factors, which may be used to select appropriate values for the distances $L_1$–$L_4$.

The width (diameter in three-dimensional case) $W_1$ of the flux concentrator is dependent upon the width of the corresponding side of the sensor element 4.3. The width (diameter) $W_1$ is generally provided a minimum of three times the width of the sensor element 4.3. The width (diameter) $W_1$ is a function of the length $L_2$ such that the smaller the distance $L_2$, the closer the width (diameter) $W_1$ becomes to the minimum width (diameter) of three times the sensor element width. The width (diameter) $W_2$ is selected to provide a particular gain characteristic for a planar device as shown. Gain is provided as the ratio of $W_2$ to $W_1$.

It should be noted that the illustrative fiber optic magnetic field or current sensor design in FIG. 11 is based on the Malus interferometer scheme, which is simpler than Sagnac interferometer scheme. From another point of view, the Sagnac interferometer scheme is known as the more stable [Rose A. H. "Playing with fire and fibers." IEEE Circuits and Devices Magazine, vol. 15, (no. 5), IEEE, September 1999. p. 41].

Figure 12:
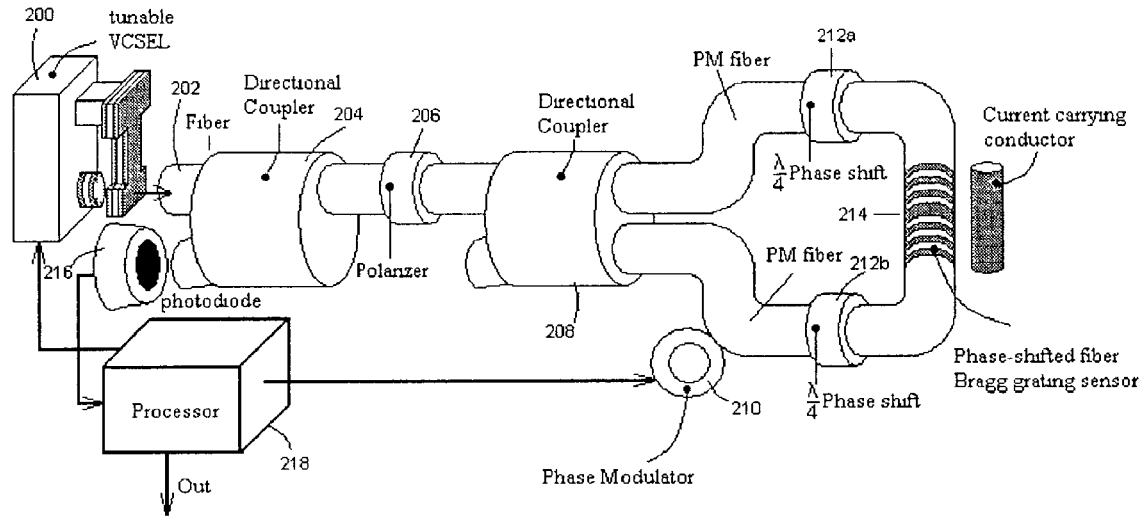
FIG. 12 shows an illustrative Sagnac interferometer method of the magneto-optical sensing system.

Referring now to FIG. 12, the body of an illustrative Sagnac interferometer current sensor is constructed from a polarization maintaining fiber. A tunable light source 200 such as, for example, a tunable VCSEL generates a light that is coupled into the fiber 202. The light passes through a directional coupler 204 and is linearly polarized by a fiber polarizer 206. The linearly polarized light is then coupled into the loop portion of the sensor as two counter-propagating, linearly polarized light waves by another directional coupler 208. The phase modulator 210 applies a periodic signal in order to modulate the phase or dither the light waves. Just before the two light waves enter the sensor itself, they pass through two quarter-wave plates 212*a*, 212*b*, oriented with the principle axes at 45 degrees with respect to the axes of the polarization maintaining fiber of the Sagnac interferometer.

Immediately following the quarter-wave plates is a phase-shifted fiber Bragg grating 214, preferably made from a low birefringence fiber. The purpose of the quarter-wave plates is to convert the linearly polarized light from the polarization maintaining fiber of the Sagnac loop to circularly polarized light. There is no fundamental advantage to using right or left handed circularly polarized light in the region of the phase-shifted Bragg grating 214. Exiting the region of the phase-shifted Bragg grating 214, one light wave continues on and passes through the quarter-wave plate 212*b*, and the other light wave passes through the other quarter-wave plate 212*a*. The quarter-wave plates 212 now convert both light waves back to linearly polarized light aligned with the polarization maintaining fiber polarization axes of the Sagnac loop. The returning light waves pass through directional couplers 208, 204, and directed toward the photodetector 216, which provides an output signal to the signal processor 218. The signal processor then generates an output indicative of the magnitude of the current flowing in the current carrying conductor.

Quarter-wave plate non-idealities, either arising from angular misalignments or from deviations from quarter-wave operation, create only second order errors in the sensor output. Quarter-wave plate error causes light to be coupled to the unused axis of the polarization maintaining fiber of the Sagnac loop, but such light is eventually rejected by the polarizer in its common input/output port.

Fiber-optic quarter-wave plates may be constructed from a low birefringence fiber wound around a relatively small diameter rod. However, the quality of quarter-wave plates constructed in this manner has been shown to be poor. An alternative is to use a short length of polarization maintaining fiber. The polarization beat length of the polarization maintaining fiber is preferably long enough to facilitate splicing this fiber between the Sagnac loop fiber and the fiber in which phase-shifted Bragg grating is written.

Such designs of magnetic field sensor and instruments may not be suitable under certain circumstances for low magnetic field (pT–μT range) detection due to too low Verdet constant of the glass. From another point of view, yttrium iron garnet (YIG) is known to be the best material for low magnetic field magneto-optical sensing due to its extremely high Faraday constant for the transparent materials. The best YIG materials have a Faraday rotation at 1550 nm on the order of 3000 deg/cm Oe for in-plane fields [Hyonju Kim, Grishin A. M., Rao K. V., Yu S. C., Sbiaa R., Le Gall H., "Ce-substituted YIG films grown by pulsed laser deposition for magneto-optic waveguide devices", IEEE Transactions on Magnetics, vol. 35, (no. 5, pt. 1), IEEE, September 1999. p. 3163; Wallenhorst M., Niemoller M., Dotsch H., Hertel P., Gerhardt, R., Gather B. "Enhancement of the nonreciprocal magneto-optic effect of TM modes using iron garnet double layers with opposite Faraday rotation", Journal of Applied Physics, vol. 77, (no. 7), 1 Apr.1995. p. 2902; Kamada O., Minemoto H., Itoh N., "Magnetooptical Properties Of $(BiGdY)_3Fe_5O_{12}$ For Optical Magnetic-field Sensors", Journal Of Applied Physics, 75: (10) 6801–6803, Part 2B May 1994]. The detectivity limit was demonstrated in the range of $pT/Hz^{1/2}$, where flux concentrators have been employed [Deeter M. N. "Fiber-optic Faraday-effect magnetic-field sensor based on flux concentrators", Applied Optics, vol. 35, (no. 1), January 1996. p. 154]. YIG waveguides are well known and suggested for use both in optical isolators and magnetic field sensors.

Figure 13:
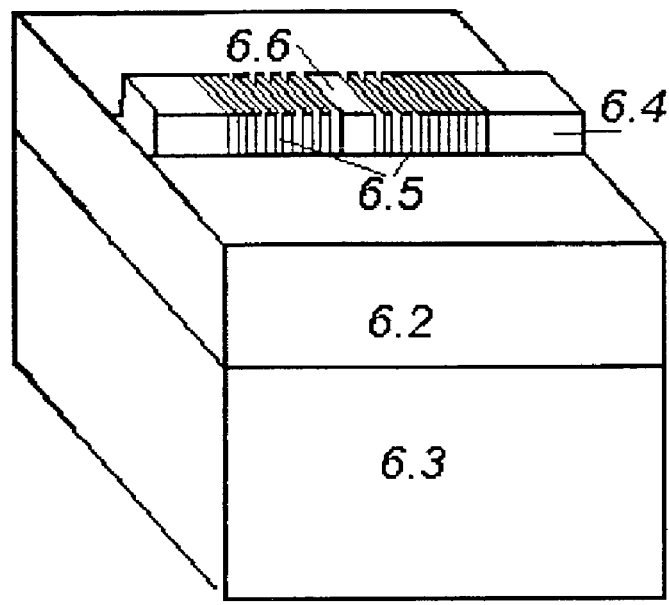
FIG. 13 is an isometric view of an illustrative magneto-optic sensing element utilizing magnetic garnet waveguide.

Referring now to FIG. 13, an illustrative magneto-optic sensing element 6.1 is provided by the magnetic garnet layer 6.2 with thickness in the range of 0.4–3 microns grown on the GGG (Gadolinium Gallium Garnet) substrate 6.3 by liquid phase epitaxy (LPE), by sol gel or by any other technique known to those of ordinary skill in the art. The magnetic garnet single crystal is having a composition formula expressed by $R_{3-x}Md_xFe_{5-v-w-y}Ma_vMb_wMc_yO_{12}$ where R indicates a rare earth element including yttrium, Ma is a trivalent cationic element, Mb is a tetravalent cationic element; Mc is a transition element and x, y, v and w satisfy the following relationships: $0.6 \leq x \leq 3$; $0 \leq y \leq \leq 0.47$; $0 \leq v \leq 1.0$; $0 \leq w \leq 0.35$. R is one kind or two or more kinds of rare earth elements selected from a group consisting of Y, La, Lu, Tb and Gd. Ma is one kind or two or more kinds of trivalent cationic elements selected from a group consisting of Al, Ga and In. Mb is one kind or two or more kinds of tetravalent cationic elements selected from a group consisting of Ge, Sn, Ti, Zr, and Si. Md is one kind or two kinds of elements selected from group consisting of Bi and Ce.

The magnetic garnet layer 6.2 may be provided such that the total magnetic free energy of the layer is anisotropic with respect to the orientation of the magnetization vector in the layer plane. This anisotropic total magnetic free energy dependence on magnetization orientation can be described by assuming the presence of a (fictitious) in-plane uniaxial anisotropy field. Here the magnetic layer may be provided with a small, spatially homogeneous in-plane uniaxial anisotropy.

The presence of the in-plane uniaxial anisotropy field defines an axis along which a magnetization vector of the magnetic garnet layer 6.2 lies prior to the application of an external stimulus to be measured. Said axis is generally referred to as a so-called "easy axis." Orthogonal to the easy axis is a so-called "hard axis" along which the total magnetic field free energy is maximized, so it is most energetically unfavorable for the magnetization to lie along the hard axis. The direction of the magnetization vector should preferably not deviate from the easy axis unless external stimuli are applied to the magnetic garnet layer 6.2 at an angle relative to the easy axis.

The orientation of the magnetization in the plane of the magnetic garnet layer is responsive to application of external magnetic fields in the film plane, so the magneto-optic sensing element 6.1 may be disposed to provide a magnetic field sensor, or electrical current sensor, for example.

If other magnetic garnet film characteristics (e.g., magneto-optic constant, optical absorption, film thickness, film composition, etc.) are provided having predetermined values, the amount of rotation of the magnetization in the film plane with a fixed applied stimulus (magnetic field, current, etc.) depends upon the magnitude of the in-plane uniaxial anisotropy in the magnetic layer and the angle at which the stimuli is applied relative to the easy axis. The sensitivity of the sensor depends upon the degree of magnetization rotation for an incremental change in applied stimuli. Thus, a trade off may exist between sensor sensitivity and the range of a particular quantity, that can be measured by the sensor. Such a trade off can affect the selection of a particular in-plane uniaxial anisotropy field.

For example, if the magneto-optic sensing element 6.1 is disposed to provide a magnetic field sensor, and the in-plane uniaxial anisotropy field is provided having a value of ten oersteds (Oe), then magnetic fields having a value greater than ten Oe will saturate a sensor provided from the magneto-optic sensing element 6.1 and thus may not be measured. It should be noted that the provision of different in-plane uniaxial fields may provide such a sensor having optimum characteristics for different applications.

It would also be desirable for the magnetic garnet layer 6.2 to be provided having a large Faraday constant at the operational wavelength. The sensitivity of an optical detection system (not shown) increases with the Faraday constant, if all other film characteristics and stimuli are held constant.

It is further desirable that the optical absorption of the magnetic garnet layer 6.2 be small at the operational wavelength, in order to minimize the losses in the waveguide. As will be disclosed further below, optimizing the total sensitivity of a sensor system may involve tradeoffs between the magnetic garnet layer 6.2 having a low optical absorption and a large Faraday constant.

The rib waveguide 6.4 is formed on the top of magnetic garnet single crystal layer by deposition of $SiO_2$, polymer or any other material transparent at the operational wavelength range of the said sensor known to those of ordinary skill in the art by sputtering, deposition, spin-coating or any technique well known to those of ordinary skill in the art. The rib is formed by photolithographic patterning, followed by etching or any technique well known to those of ordinary skill in the art. The waveguide Bragg grating 6.5 is written into the rib layer 6.4 by photolithographic patterning, followed by reactive ion etching (RIE) or any other technique known to those of ordinary skill in the art. The Bragg grating 6.5 should have at least one phase shift 6.6, equal to the integer multiple of $\pi$. It is desirable that the length of the grating and other parameters are choused so that the light traveling through the waveguide and having a wavelength corresponding to maximum transmission within the phase shift corresponded maximum in Bragg transmission minimum, is travel the maximum possible effective distance through the Bragg grating.

When a projection of a magnetic field (or magnetic field generated by electrical current) in the rib direction is present in the position of the magneto-optic sensing element 6.1, the magnetic garnet layer will gain some magnetization in the direction of the rib and the waveguide will exhibit the Faraday effect (i.e., polarization state of light sent through the rib waveguide will be altered through the TE→TM and/or TM→TE mode conversion). Since the effective distance traveled by the light through the waveguide with the phase-shifted Bragg grating written in it, at the wavelength of transmission maximum corresponding to the phase shift (see FIG. 2), far exceeds (by orders of magnitude) the physical length of the Bragg grating itself, the effective Faraday rotation at this wavelength will also be enhanced proportionally to the enhancement of the effective length traveled by the light.

It also should be noted that the uniform bias field can be applied in the plane of the magnetic garnet layer 6.2 to eliminate domain boundaries. Such a bias field can be produced, for example, by placing a flat, large area permanent magnet under or above the magneto-optic sensing element 6.1 or by sputtering a thin (100–2000 nm) layer of high-coercivity magnetic material on the bottom side of GGG substrate by magnetron sputtering or any other technique known to those of ordinary skill in the art.

Further Description of an Embodiment

A phase-shifted FBG was purchased from a commercial supplier (O/E-Land, Ltd.). The physical length of this FBG was 2.5 cm and it was designed to have one phase shift exactly in the middle of the FBG. A FBG was written into common circular-core single-mode photosensitive (i.e., with Ge: doped core material) fiber, which are used for optical communications. The transmission spectrum of the FBG was measured at the polarization of the incident light at no applied magnetic field with New Focus Vidia-swept model #6428 tunable laser source and a Newport photoreceiver.

Figure 14:
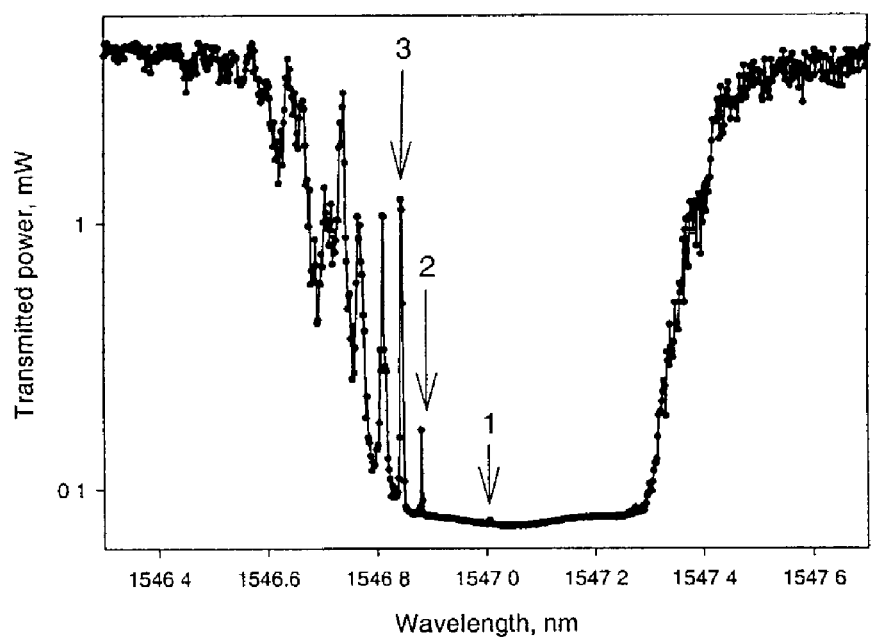
FIG. 14 shows an exemplary transmission spectrum of an experimental phase-shifted fiber Bragg grating sensor apparatus used to measure magnetic fields.

FIG. 14 shows the result of such measurements. The transmission spectrum contains multiple peaks within the wide transmission valley instead of just one peak, as the design predicted (see FIGS. 2a, 6a, etc.). Most probably it was because of nonuniformity of the exposure during the FBG writing.

Figure 15:
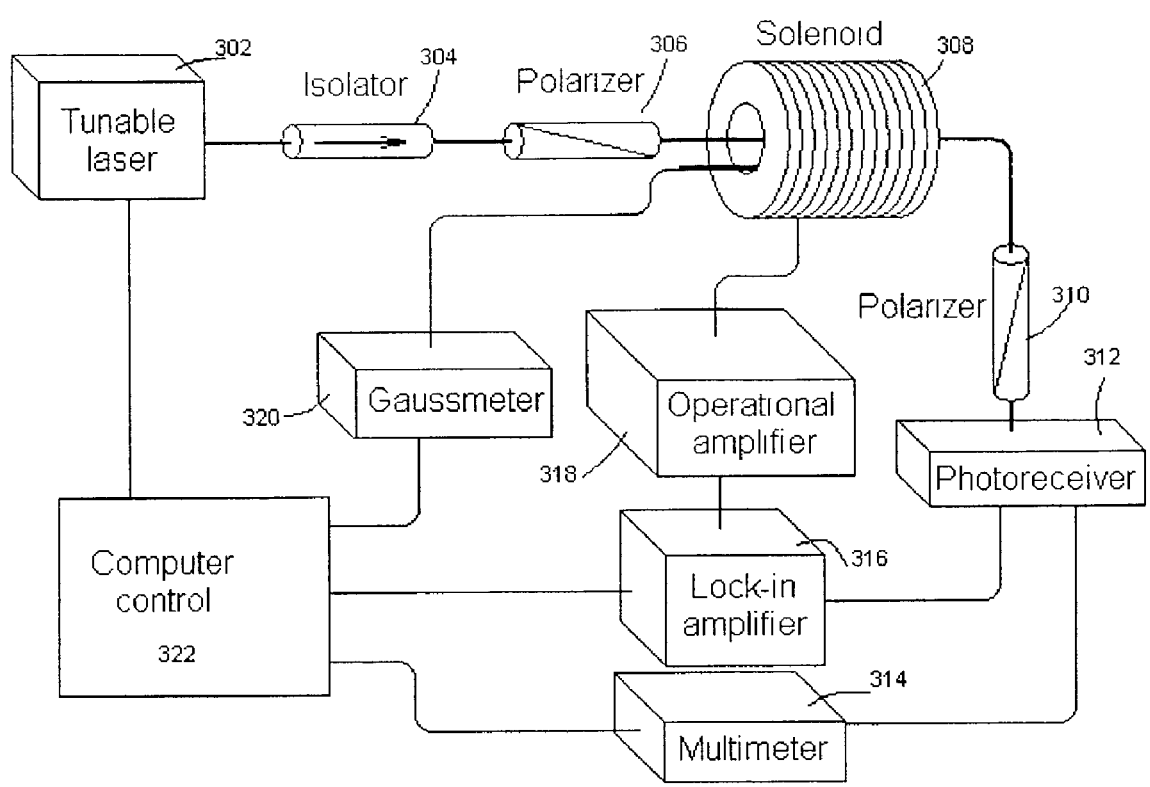
FIG. 15 shows an exemplary illustrative experimental sensing apparatus.

To examine the spectral dependence of the Faraday rotation of such a FBG the experimental setup 300 was constructed, which is schematically shown in FIG. 15. The same New Focus tunable laser 307 was used as a light source. The isolator 304 was placed right after the laser to insure that the light back-reflected by the FBG would not affect the laser output characteristics. The polarizer 306 was disposed between the isolator. The FBG (not shown) was mounted in the 30-cm long solenoid electromagnet 308 along the axis of said solenoid so the magnetic field generated by the solenoid was collinear to the fiber. The second polarizer 310 (the analyzer) was disposed between the FBG and the photoreceiver 312 (New Focus Nirvana photoreceiver Model 2017). The polarizer and analyzer 310 were oriented so the angle between the polarization axes of said polarizer and analyzer was about 80 degrees. The voltage output from the photoreceiver 312 was equally divided between the multimeter 314 and the input of the lock-in amplifier 316 (Stanford Research Systems, Model #SR 830 DSP). The output from the lock-in amplifier 316 was connected to the Kepco bipolar operational amplifier 318, which, in turn, was connected to the solenoid. The magnetic field in the solenoid 308 was actively measured by a gaussmeter 320. Tunable laser 302, lock-in amplifier 316, multimeter 314 and gaussmeter 320 were connected through GPIB port to the computer 322. By using such an experimental setup, the voltage from the lock-in amplifier 316 was converted into the current oscillations in the solenoid 308 by operational amplifier 318, causing the oscillations of the magnetic field at the position of the FBG. The value of such oscillations was independently monitored by the gaussmeter 320.

Figure 16A:
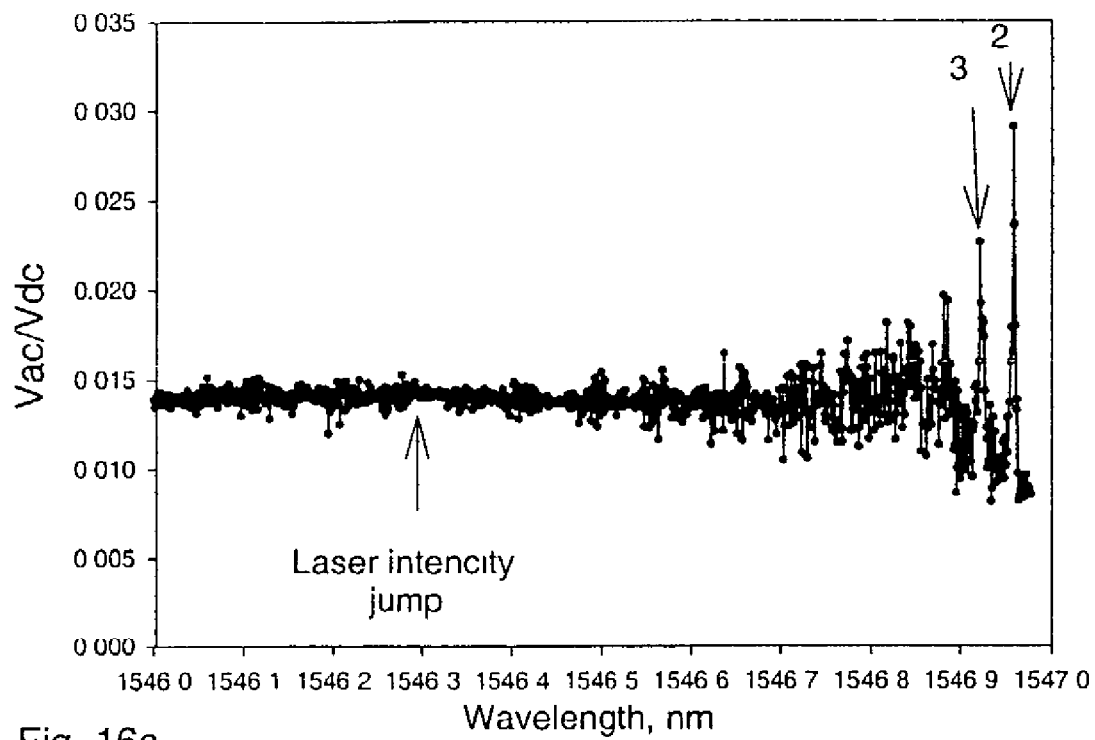
FIGS. 16A and 16B show exemplary measured spectral dependencies.
Figure 16B:
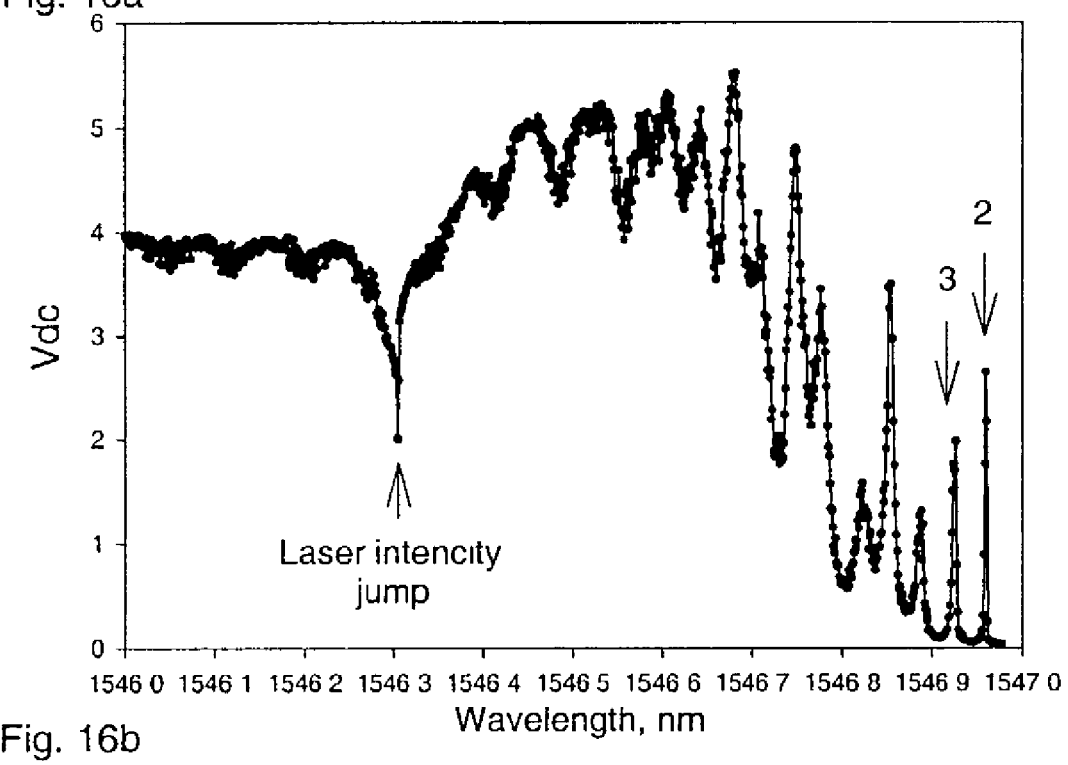

A 50 Hz AC magnetic field (100 Oe RMS) was used. The measured spectral dependences of $V_{AC}/V_{DC}$ are shown in FIG. 16a and $V_{DC}$ are shown in FIG. 16b. DC voltage was the signal from the multimeter 314 with averaging over at least 10 current oscillations, while the $V_{AC}/V_{DC}$ ratio was the ratio taken from lock-in amplifier 316 and multimeter 314. The $V_{AC}/V_{DC}$ ratio is proportional to $\tan\theta_F$ (where $\theta_F$ is the magnetic field-induced polarization rotation in the fiber), and for such a small angles can be considered to be proportional to the $\theta_F$. Without applied magnetic field (i.e., when the output from operational amplifier 308 was disconnected from the solenoid), the $V_{AC}$ and hence $V_{AC}/V_{DC}$ were equal to 0. The normalization of the AC voltage was used to read of the intensity jumps from the laser. The effectiveness of such a normalization is shown in FIGS. 16a and 16b. A strong laser intensity jump occurred at 1546.3 nm, which is clearly detected by $V_{DC}$ (FIG. 16b). On the $V_{AC}/V_{DC}$ transmission spectrum (FIG. 16a) this jump is completely compensated by the normalization. We can thus state that peaks and valleys in FIG. 16a are caused by the magnetic field, not intensity variations.

Figure 17A:
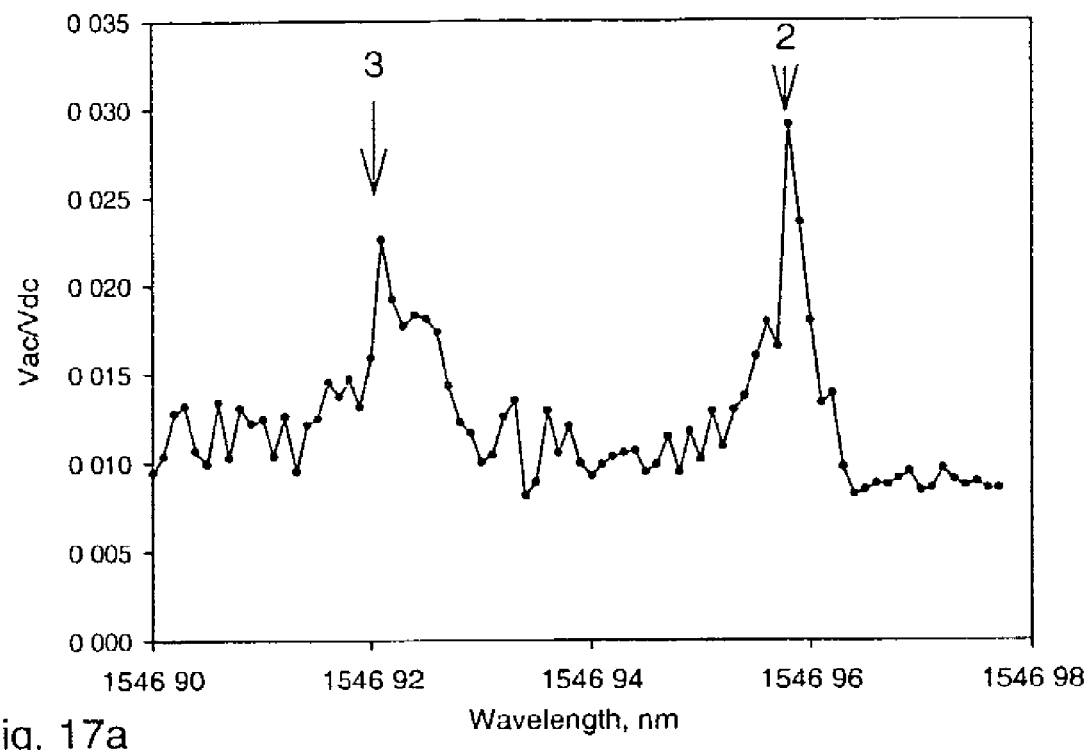
FIGS. 17A and 17B show additional exemplary measured spectral dependencies.
Figure 17B:
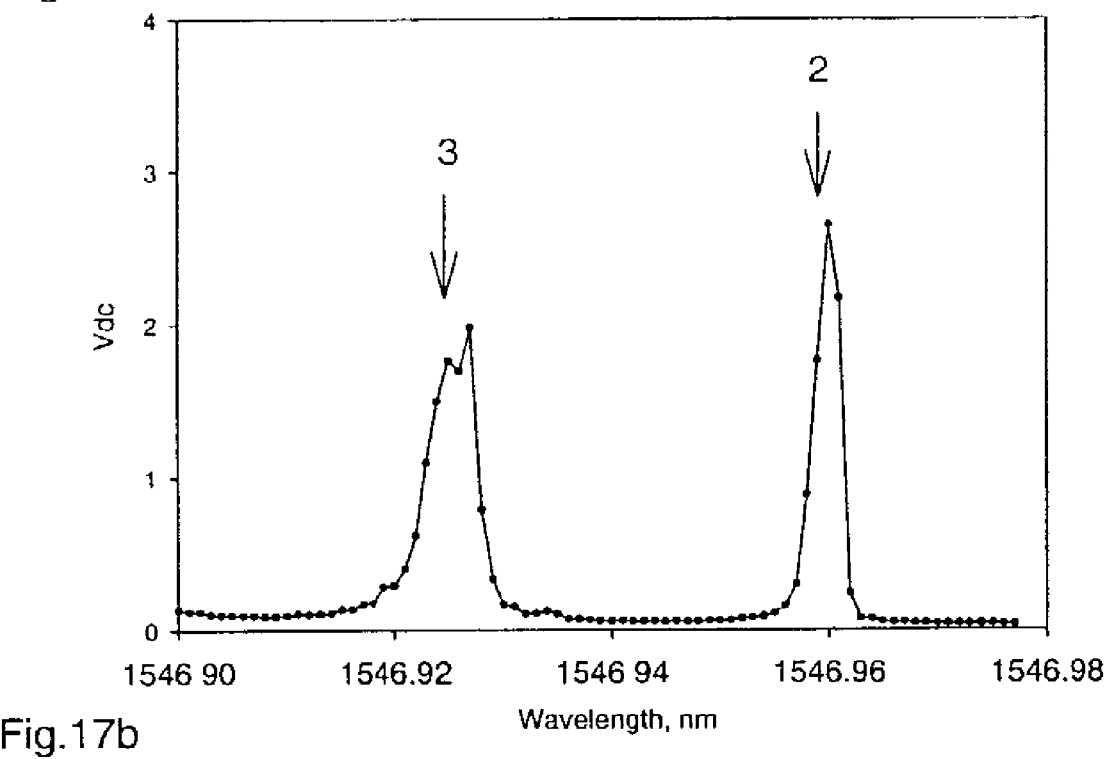

As follows from FIGS. 16a and 16b, the polarization rotation indeed experienced enhancement at the wavelengths of the phase-shift-induced transmission peaks. FIGS. 17a, 17b show the magnified views of the peaks of $V_{AC}/V_{DC}$ and $V_{DC}$ respectively. For convenience, the peaks of polarization rotation and transmittance are numbered in FIGS. 14, 16a–16b and 17a–17b. As follows from FIGS. 16a, 16b, 17a, 17b, the polarization rotation enhancement is observed for all phase-shift induced transmission peaks. However, the maximum enhancement is obtained for peaks 2 and 3. For peak number 2 the enhancement factor is 2. Now we should recall that the physical length of the FBG was only 2.5 cm, while the length of the fiber that was exposed to the magnetic field in the solenoid exceeded 30 cm (length of the solenoid wire coils). I.e., the real enhancement factor was 30 over 2.5 cm length of FBG. The highest enhancement factor for the peak number 2 can be explained by the highest quality of the transmittance resonance corresponding to this peak.

While the invention has been disclosed in connection with what is presently considered to be the most practical and preferred embodiment, it is to be understood that the invention is not to be limited to the disclosed embodiment, but on the contrary, is intended to be illustrative of various modifications and equivalent arrangements included within the scope of the appended claims.

We claim:

1. Apparatus for detecting a magnitude of a physical parameter, the apparatus comprising:
   a light source;
   a magneto-optic Faraday effect sensing element comprising a fiber phase shifted Bragg grating;
   a first polarizer disposed between light source and said magneto-optic Faraday effect sensing element;
   a second polarizer (analyzer) optically coupled to the magneto-optic Faraday effect sensing element to detect the appearance of a polarization state different from the one transmitted through the first polarizer; and
   an optical detector optically coupled to the second polarizer.

2. An apparatus as in claim 1 wherein the light source comprises a tunable laser.

3. An apparatus as in claim 2 wherein the light source comprises a tunable VCSEL.

4. An apparatus as in claim 1 wherein the light source comprises a broad band light source, and the apparatus may include a circulator and fiber Bragg gratings or other wavelength filters, the filtering reflection characteristics of which coincide with the Bragg grating optical feature of the sensing element.

5. An apparatus as in claim 1 wherein the light source comprises a broadband light source chosen from the group, consisting of a light emitting diode (LED), a Superluminescent diode (SLD) and a lamp.

6. An apparatus as in claim 1 wherein the detector is chosen from the group consisting of a semiconductor photodiode and a balanced photodetector employing two photodiodes and a polarizing beam splitter.

7. An apparatus as in claim 6 wherein the detector comprises plural photodiodes with a polarization splitter to detect orthogonal polarization components transmitted through the sensing element light.

8. An apparatus as in claim 1 wherein the physical parameter is at least one selected from the group consisting of a magnetic field and the magnetic field generated by an electrical current, utilized to determine the electrical current characteristics.

9. An apparatus as in claim 1 herein the phase-shifted fiber Bragg grating is written into fiber and is selected from the group consisting of communication single-mode fiber with symmetrical core (low birefingence), a polarization-maintaining single-mode fiber with highly asymmetric core (high-birefringence), and a specifically formulated high Verdet constant glass fiber.

10. An apparatus as in claim 1 wherein the phase-shifted fiber Bragg grating comprises a constant-period Bragg grating.

11. An apparatus as in claim 1 is constructed from two or more superimposed phase-shifted Bragg gratings to compensate for birefringence.

12. An apparatus as in claim 1 wherein the phase-shifted fiber Bragg grating uses at least one phase shift.

13. An apparatus as in claim 1 further including an environmental effects compensation feedback arrangement and wherein said light source comprises a tunable laser coupled to said feedback arrangement.

14. An apparatus as in claim 1 wherein the magneto-optic Faraday effect sensing element includes flux concentrators that increase the magnitude of the magnetic field in the positions of the phase shift(s).

15. A method for detecting a magnitude of a physical condition, comprising:
    applying polarized light to a magneto-optic Faraday effect sensing element comprising a fiber phase-shifted Bragg grating; and
    analyzing light received from said fiber phase shifted Bragg grating to detect the appearance of a polarization state different from the first one.

* * * * *